US011395638B2

(12) United States Patent
Shin et al.

(10) Patent No.: US 11,395,638 B2
(45) Date of Patent: Jul. 26, 2022

(54) INTERLEAVED TRANSMIT SEQUENCES AND MOTION ESTIMATION IN ULTRASOUND IMAGES, AND ASSOCIATED SYSTEMS, DEVICES, AND METHODS

(71) Applicant: KONINKLIJKE PHILIPS N.V., Eindhoven (NL)

(72) Inventors: Jun Seob Shin, Medford, MA (US); Francois Guy Gerard Marie Vignon, Andover, MA (US); David Hope Simpson, Bothell, WA (US); Andrew Hancock, Sacramento, CA (US); Sheng-Wen Huang, Ossining, NY (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 156 days.

(21) Appl. No.: 16/733,286

(22) Filed: Jan. 3, 2020

(65) Prior Publication Data

US 2020/0214663 A1 Jul. 9, 2020

Related U.S. Application Data

(60) Provisional application No. 62/789,226, filed on Jan. 7, 2019.

(51) Int. Cl.

*A61B 8/12* (2006.01)
*A61B 8/00* (2006.01)
*A61B 8/08* (2006.01)

(52) U.S. Cl.

CPC .............. *A61B 8/12* (2013.01); *A61B 8/0891* (2013.01); *A61B 8/4488* (2013.01); *A61B 8/5207* (2013.01); *A61B 8/54* (2013.01)

(58) Field of Classification Search

CPC ....... A61B 8/12; A61B 8/0891; A61B 8/4488; A61B 8/5207; A61B 8/54; A61B 8/5253;
(Continued)

(56) References Cited

U.S. PATENT DOCUMENTS 6,520,915 B1 2/2003 Lin
6,620,103 B1 9/2003 Bruce
(Continued)

FOREIGN PATENT DOCUMENTS

WO 200030541 A1 6/2000

OTHER PUBLICATIONS

Kasai, Chihiro et al, "Real-Time Two-Dimensional Blood Flow Imaging Using an Autocorrelation Technique," IEEE Transactions on Sonics and Ultrasonics, vol. SU-32, No. 3, May 1985.

*Primary Examiner* — Joseph M Santos Rodriguez
*Assistant Examiner* — Kaitlyn E Sebastian

(57) ABSTRACT

Systems, methods, and devices that perform flow scan sequences are provided. In one embodiment, an ultrasound imaging system includes an intraluminal catheter or guidewire, an annular array of acoustic elements positioned around a circumference of the catheter or guidewire, and a processor in communication with the annular array. The processor is configured to activate a first subaperture of the annular array at a first time, thereafter, activate a second interleaving subaperture, and activate the first subaperture again at a different, second time such that the scan sequence moves around the circumference of the catheter or guidewire. Temporal differences between the received ultrasound signals obtained by the first subaperture at the first and second times are determined to detect motion around the annular array. By interleaving subaperture firings, the total number of firings to form an image frame can be reduced.

21 Claims, 16 Drawing Sheets

(58) Field of Classification Search
CPC ..... A61B 8/5246; A61B 8/4494; A61B 8/488; A61B 8/4461; A61B 8/06
See application file for complete search history.

(56) References Cited

U.S. PATENT DOCUMENTS

| | | | | |
|---|---|---|---|---|
| 6,776,763 | B2 | 8/2004 | Nix | |
| 7,226,417 | B1 | 6/2007 | Eberle | |
| 2006/0036175 | A1 | 2/2006 | Guracar | |
| 2010/0036249 | A1 | 2/2010 | Clark | |
| 2011/0016977 | A1 | 1/2011 | Guracar | |
| 2011/0054316 | A1 | 3/2011 | Kristoffersen | |
| 2014/0018680 | A1 | 1/2014 | Guracar | |
| 2014/0056099 | A1* | 2/2014 | Hancock | A61B 8/445 367/11 |
| 2015/0087986 | A1* | 3/2015 | Nair | G01S 7/52074 600/447 |
| 2015/0305710 | A1 | 10/2015 | Stigall | |
| 2016/0007947 | A1* | 1/2016 | Spencer | A61B 8/0841 600/424 |
| 2016/0121142 | A1 | 5/2016 | Zhang | |

* cited by examiner

| | | | | | | | | | | | | | | | | | | | | | |
|---|---|---|---|---|---|---|---|---|---|---|---|---|---|---|---|---|---|---|---|---|---|
| 18 | | | | | 70 | 72 | 96 | 102 | 122 | 132 | 148 | 162 | 174 | 192 | 200 | 222 | 226 | 252 | | | |
| 19 | | | | | | 71 | 97 | 101 | 123 | 131 | 149 | 161 | 175 | 191 | 201 | 221 | 227 | 251 | 253 | | |
| 20 | | | | | | | 98 | 100 | 124 | 130 | 150 | 160 | 176 | 190 | 202 | 220 | 228 | 250 | 254 | 280 | |
| 21 | | | | | | | | 99 | 125 | 129 | 151 | 159 | 177 | 189 | 203 | 219 | 229 | 249 | 255 | 279 | 281 |
| 22 | | | | | | | | | 126 | 128 | 152 | 158 | 178 | 188 | 204 | 218 | 230 | 248 | 256 | 278 | 282 |
| 23 | | | | | | | | | | 127 | 153 | 157 | 179 | 187 | 205 | 217 | 231 | 247 | 257 | 277 | 283 |
| 24 | | | | | | | | | | | 154 | 156 | 180 | 186 | 206 | 216 | 232 | 246 | 258 | 276 | 284 |
| 25 | | | | | | | | | | | | 155 | 181 | 185 | 207 | 215 | 233 | 245 | 259 | 275 | 285 |
| 26 | | | | | | | | | | | | | 182 | 184 | 208 | 214 | 234 | 244 | 260 | 274 | 286 |
| 27 | | | | | | | | | | | | | | 183 | 209 | 213 | 235 | 243 | 261 | 273 | 287 |
| 28 | | | | | | | | | | | | | | | 210 | 212 | 236 | 242 | 262 | 272 | 288 |
| 29 | | | | | | | | | | | | | | | | 211 | 237 | 241 | 263 | 271 | 289 |
| 30 | | | | | | | | | | | | | | | | | 238 | 240 | 264 | 270 | 290 |
| 31 | | | | | | | | | | | | | | | | | | 239 | 265 | 269 | 291 |
| 32 | | | | | | | | | | | | | | | | | | | 266 | 268 | 292 |
| 33 | | | | | | | | | | | | | | | | | | | | 267 | 293 |
| 34 | | | | | | | | | | | | | | | | | | | | | 294 |

| Index | Subaperture index firing sequence | |
|---|---|---|
| 1 | 1111111111111111111111111111111111111111111111111111111111111111 (64x) | |
| 2 | 2222222222222222222222222222222222222222222222222222222222222222 (64x) | |
| 3 | 3333333333333333333333333333333333333333333333333333333333333333 (64x) | |
| ... | ... | |
| 64 | 64 64 64 64 64 64 64 64 64 64 64 64 64 64 64 64 64 64 64 64 64 64 64 64 64 64 64 64 64 64 64 64 64 64 64 64 64 64 64 64 64 64 64 64 64 64 64 64 64 64 64 64 64 64 64 64 64 64 64 64 64 64 64 64 (64x) | |
| Total firings: 4096 | Interval PRI: 1 firing | Ensemble length: 64 |

| Pass | Subaperture index firing sequence | |
|---|---|---|
| 1 | 123456789...64<br>101 | |
| 2 | 123456789...64 | |
| 3 | 123456789...64 | |
| ... | ... | |
| N | 123456789...64 | |
| Total firings: 64 x N | Interval PRI: 64 | Ensemble length: N |

| Group | Subaperture index firing sequence | |
|---|---|---|
| 1 | 1234 1234 1234 1234 1234 1234 1234 1234 (8x)<br>201 | |
| 2 | 5678 5678 5678 5678 5678 5678 5678 5678 (8x) | |
| 3 | 9 10 11 12 9 10 11 12 9 10 11 12 9 10 11 12<br>9 10 11 12 9 10 11 12 9 10 11 12 9 10 11 12 (8x) | |
| ... | ... | |
| 16 | 61 62 63 64 61 62 63 64 61 62 63 64 61 62 63 64<br>61 62 63 64 61 62 63 64 61 62 63 64 61 62 63 64 (8x) | |
| Total firings: 512 | Interval PRI: 4 firings | Ensemble length: 8 |

| Group | Subaperture index firing sequence | |
|---|---|---|
| 1 | 1 5 9 13  1 5 9 13  1 5 9 13  1 5 9 13  1 5 9 13  1 5 9 13  1 5 9 13  1 5 9 13 (8x) | |
| 2 | 2 6 10 14  2 6 10 14  2 6 10 14  2 6 10 14  2 6 10 14  2 6 10 14  2 6 10 14  2 6 10 14 (8x) | |
| 3 | 3 7 11 15  3 7 11 15  3 7 11 15  3 7 11 15  3 7 11 15  3 7 11 15  3 7 11 15  3 7 11 15 (8x) | |
| ... | ... | |
| 16 | 52 56 60 64  52 56 60 64  52 56 60 64  52 56 60 64<br>52 56 60 64  52 56 60 64  52 56 60 64  52 56 60 64 (8x) | |
| Total firings: 512 | Interval PRI: 4 firings | Ensemble length: 8 |

| Pass | Subaperture index firing sequence | |
|---|---|---|
| 1 | 1 5 9 13 17 21 25 29 33 37 41 45 49 53 57 61 | |
| 2 | 2 6 10 14 18 22 26 30 34 38 42 46 50 54 58 62 | |
| 3 | 3 7 11 15 19 23 27 31 35 39 43 47 51 55 59 63 | |
| 4 | 4 8 12 16 20 24 28 32 36 40 44 48 52 56 60 64 | |
| 5 | 1 5 9 13 17 21 25 29 33 37 41 45 49 53 57 61 | |
| 6 | 2 6 10 14 18 22 26 30 34 38 42 46 50 54 58 62 | |
| ... | ... | |
| N | 4 8 12 16 20 24 28 32 36 40 44 48 52 56 60 64 | |
| Total firings: 16 x N | Interval PRI: 64 firings | Ensemble length: N/4 |

<table>
<tr><th>Pass</th><th colspan="2">Subaperture index firing sequence</th></tr>
<tr><td>1</td><td colspan="2">1 6 11 16 21 26 31 36 41 46 51 56 61</td></tr>
<tr><td>2</td><td colspan="2">2 7 12 17 22 27 32 37 42 47 52 57 62</td></tr>
<tr><td>3</td><td colspan="2">3 8 13 18 23 28 33 38 43 48 53 58 63</td></tr>
<tr><td>4</td><td colspan="2">4 9 14 19 24 29 34 39 44 49 54 59 64</td></tr>
<tr><td>5</td><td colspan="2">5 10 15 20 25 30 35 40 45 50 55 60</td></tr>
<tr><td>6</td><td colspan="2">1 6 11 16 21 26 31 36 41 46 51 56 61</td></tr>
<tr><td>...</td><td colspan="2">...</td></tr>
<tr><td>N</td><td colspan="2">5 10 15 20 25 30 35 40 45 50 55 60</td></tr>
<tr><td>Total firings:(4N/5)*13+(N/5)*12</td><td>Interval PRI: 64 firings</td><td>Ensemble length: N/5</td></tr>
</table>

FIG. 15

INTERLEAVED TRANSMIT SEQUENCES AND MOTION ESTIMATION IN ULTRASOUND IMAGES, AND ASSOCIATED SYSTEMS, DEVICES, AND METHODS

CROSS-REFERENCE TO PRIOR APPLICATIONS

This application claims the benefit of U.S. Provisional Application No. 62/789,226, filed on Jan. 7, 2019, the contents of which are incorporated herein by reference.

TECHNICAL FIELD

The present disclosure relates generally to ultrasound imaging and, in particular, to detecting fluid flow motion in intraluminal ultrasound images (e.g., blood flow motion in intravascular ultrasound or IVUS images) images. For example, subapertures of an array of acoustic elements can be activated in an interleaved manner around the circumference of a catheter to obtain ultrasound data, and a processor can use determine fluid flow motion based on temporal differences of the ultrasound data.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

Solid-state (also known as synthetic-aperture) IVUS catheters are one of the two types of IVUS devices commonly used today, the other type being the rotational IVUS catheter. Solid-state IVUS catheters carry a scanner assembly that includes an array of ultrasound transducers distributed around its circumference along with one or more integrated circuit controller chips mounted adjacent to the transducer array. The controllers select individual acoustic elements (or groups of elements) for transmitting an ultrasound pulse and for receiving the ultrasound echo signal. By stepping through a sequence of transmit-receive pairs, the solid-state IVUS system can synthesize the effect of a mechanically scanned ultrasound transducer but without moving parts (hence the solid-state designation). Since there is no rotating mechanical element, the transducer array can be placed in direct contact with the blood and vessel tissue with minimal risk of vessel trauma. Furthermore, because there is no rotating element, the electrical interface is simplified. The solid-state scanner can be wired directly to the imaging system with a simple electrical cable and a standard detachable electrical connector, rather than the complex rotating electrical interface required for a rotational IVUS device.

Scanning protocols of IVUS devices can include sequences to collect data to form images of tissue, referred to as B-mode images, and to collect sequences that collect data to form flow images. For example, flow images can include power Doppler images. Flow images indicate motion in a field of view by, e.g., coloring the portion of the image exhibiting motion. Flow images can be combined with or overlaid on B-mode images to differentiate relatively stable or motionless tissue from moving blood. For example, the blood can be colored red, while the tissue is in greyscale. Accordingly, flow images can help a physician differentiate a vessel lumen from a vessel wall.

In order to collect data related to motion in addition to standard IVUS imaging data related to tissue structure, one or more flow scan sequences are interleaved with B-mode image sequences. A processor analyzes the data obtained by the flow scan sequence using a motion detection algorithm to identify changes that indicate movement of fluid and/or tissue. However, conventional flow scan sequences can require large numbers of pulses, which limits the frame rate of the flow images to, for example, 11-12 Hz). Furthermore, conventional flow scan sequences and analyses lack sensitivity to slower moving fluids.

SUMMARY

Embodiments of the present disclosure provide systems, methods, and associated devices that perform flow scan sequences overcoming one or more of the limitations described above. These flow scan sequences can be interleaved with standard imaging scan sequences (e.g. B-mode) in order to provide flow images. In one embodiment, an ultrasound imaging system includes an annular array of acoustic elements, and a processor configured to control the annular array according to a flow scan sequence. The flow scan sequence includes activating or firing an interleaving subset of subapertures between successive firings of any given sub aperture. For example, in one embodiment, a first subaperture is fired at a first time, followed by firings of a subset of different subapertures. The first subaperture is then fired at a second time, following the firings of the subset of different subapertures. Accordingly, the firings of any one subaperture are interleaved with the firings of one or more different subapertures. In some embodiments, data collected by the interleaving flow scan sequence can be analyzed using a motion detector algorithm, in contrast to the amplitude-based analysis used by some conventional flow scan sequences. The interleaving firings of the subapertures can follow a full-circle interleaving pattern, or a partial-circle interleaving pattern. By interleaving subaperture firings with the firings of other subapertures, the efficiency of the scan sequence can be improved by reducing the number of total firings required. In some embodiments, the longer interleave pulse repetition intervals between firings of any one subaperture can increase sensitivity to slower flow.

According to one embodiment, an intraluminal ultrasound imaging system includes an intraluminal catheter or guidewire, comprising a flexible elongate member configured to be positioned within a body lumen of a patient, an annular array of acoustic elements configured to transmit ultrasonic energy into an anatomy and receive echoes corresponding to the transmitted ultrasonic energy, wherein the annular array is positioned around a circumference of the flexible elongate member, and a processor in communication with the annular array. The processor is configured to activate a first subaperture of the annular array at a first time, the first subaperture comprising a subset of the acoustic elements associated with a portion of the circumference, thereafter, activate a second subaperture of the annular array, the second subaperture comprising a different subset of the acoustic elements associated with a different portion of the circumference, activate the first subaperture at a different, second time only after activating the second subaperture such that each activation in a sequence of the first and second subapertures moves around the circumference, receive ultrasound signals obtained by activating the first and second subapertures, determine temporal differences between the received ultrasound signals obtained from the first subaperture at the first and second times, and detect motion in the body lumen based on the determined temporal differences.

In some embodiments, the processor is configured to activate a plurality of subapertures, including the second subaperture, between activation of the first subaperture at the first time and the second time. In some embodiments, the processor is configured to activate the plurality of subapertures to complete at least one revolution around the annular array before activating the first subaperture at the second time. In some embodiments, the plurality of subapertures comprises all of the subapertures of the annular array except for the first subaperture. In one aspect, the plurality of subapertures comprises a non-consecutive subset of subapertures of the annular array. In another aspect, the non-consecutive subset of the subapertures comprises an interval of M subapertures, and a total number of subapertures of the annular array is divisible by M. In still another aspect, the non-consecutive subset of the subapertures comprises an interval of M subapertures, and a total number of subapertures of the annular array is not divisible by M.

In some embodiments, the processor is configured to activate the plurality of subapertures to complete only part of a revolution around the annular array before activating the first subaperture at the second time. In some embodiments, the processor is further configured to activate the first subaperture at a third time and a fourth time, wherein the third time is after the first time and the fourth time is after the second time, average the received ultrasound signals obtained by the first subaperture at the first time and the third time, and average the received ultrasound signals obtained by the first subaperture at the second time and the fourth time. In some embodiments, the processor is further configured to activate an imaging sequence to generate an ultrasound image, generate a flow map based on the detected motion, modify the ultrasound image based on the flow map, and output the modified ultrasound image to a display.

According to another embodiment of the present disclosure, a method for detecting motion in a body lumen includes controlling, by a processor, an annular array of acoustic elements in communication with the processor to perform a scan sequence, wherein the annular array is coupled to a distal portion of a flexible elongate member configured to be positioned within the body lumen, and wherein activating the scan sequence comprises, activating a first subaperture of the annular array at a first time, wherein the first subaperture comprises a subset of the acoustic elements associated with a portion of the circumference, thereafter, activating a second subaperture of the annular array, wherein the second subaperture comprises a different subset of the acoustic elements associated with a different portion of the circumference, activating the first subaperture at a different, second time only after activating the second subaperture such that each activation in a sequence of the first and second subapertures moves around the circumference, receiving, at the processor, ultrasound signals obtained by activating the first and second subapertures, determining differences in phase between the received ultrasound signals obtained from the first subaperture at the first and second times, and detecting motion in the body lumen based on the determined differences in phase.

In some embodiments, activating the scan sequence further comprises activating a plurality of subapertures, including the second sub aperture, between activating the first subaperture at the first time and the second time. In some embodiments, activating the plurality of subapertures comprises activating the plurality of subapertures to complete at least one revolution around the annular array before activating the first subaperture at the second time. In some embodiments, activating the plurality of subapertures comprises activating all of the subapertures of the annular array except for the first subaperture. In one aspect, activating the plurality of subapertures comprises activating a non-consecutive subset of subapertures of the annular array. In another aspect, the non-consecutive subset of the subapertures comprises an interval of M subapertures, and a total number of subapertures of the annular array is divisible by M. In still another aspect, the non-consecutive subset of the subapertures comprises an interval of M subapertures, and a total number of subapertures of the annular array is not divisible by M.

In some embodiments, activating the plurality of subapertures includes activating the plurality of subapertures to complete only part of a revolution around the annular array before activating the first subaperture at the second time. In some embodiments, the method further includes activating the first subaperture at a third time and a fourth time, wherein the third time is before the first time and the fourth time is after the second time, averaging the received ultrasound signals obtained by the first subaperture at the first time and the third time, and averaging the received ultrasound signals obtained by the first subaperture at the second time and the fourth time. In some embodiments, the method further includes activating an imaging sequence to generate an ultrasound image, generating a flow map based on the detected motion, modifying the ultrasound image based on the flow map, and outputting the modified ultrasound image to a display.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 7 is a diagrammatic view of a flow scan sequence, according to aspects of the present disclosure.

FIG. 11 is a diagrammatic view of a full-circle interleave flow scan sequence, according to aspects of the present disclosure.

FIG. 12 is a diagrammatic view of a partial-circle interleave flow scan sequence, according to aspects of the present disclosure.

FIG. 13 is a diagrammatic view of a partial-circle interleave flow scan sequence, according to aspects of the present disclosure.

FIG. 14 is a diagrammatic view of a full-circle interleave flow scan sequence, according to aspects of the present disclosure.

FIG. 15 is a diagrammatic view of a full-circle interleave flow scan sequence, according to aspects of the present disclosure.

DETAILED DESCRIPTION

Figure 1:
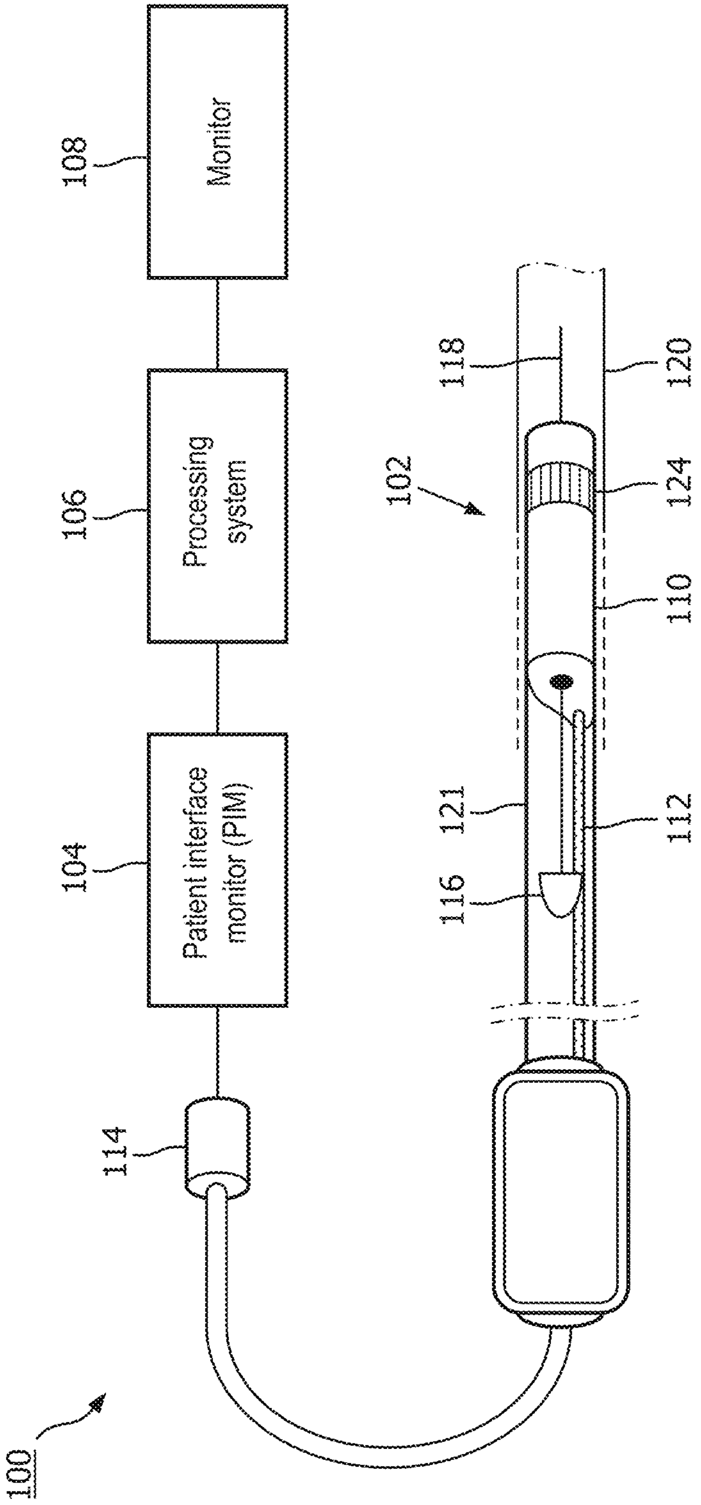
FIG. 1 is a diagrammatic schematic view of an intraluminal imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an ultrasound imaging system 100, according to aspects of the present disclosure. The ultrasound imaging system 100 can be an intraluminal imaging system. In some instances, the system 100 can be an intravascular ultrasound (IVUS) imaging system. The system 100 may include an intraluminal imaging device 102 such as a catheter, guide wire, or guide catheter, a patient interface module (PIM) 104, a processing system or console 106, and a monitor 108. The intraluminal imaging device 102 can be an ultrasound imaging device. In some instances, the device 102 can be IVUS imaging device, such as a solid-state IVUS device.

At a high level, the IVUS device 102 emits ultrasonic energy, or ultrasound signals, from a transducer array 124 included in scanner assembly 110 mounted near a distal end of the catheter device. The ultrasonic energy is reflected by tissue structures in the medium, such as a vessel 120, or another body lumen surrounding the scanner assembly 110, and the ultrasound echo signals are received by the transducer array 124. In that regard, the device 102 can be sized, shaped, or otherwise configured to be positioned within the body lumen of a patient. The PIM 104 transfers the received echo signals to the console or computer 106 where the ultrasound image (including the flow information) is reconstructed and displayed on the monitor 108. The console or computer 106 can include a processor and a memory. The computer or computing device 106 can be operable to facilitate the features of the IVUS imaging system 100 described herein. For example, the processor can execute computer readable instructions stored on the non-transitory tangible computer readable medium.

The PIM 104 facilitates communication of signals between the IVUS console 106 and the scanner assembly 110 included in the IVUS device 102. This communication includes the steps of: (1) providing commands to integrated circuit controller chip(s) 206A, 206B, illustrated in FIG. 2, included in the scanner assembly 110 to select the particular transducer array element(s), or acoustic element(s), to be used for transmit and receive, (2) providing the transmit trigger signals to the integrated circuit controller chip(s) 206A, 206B included in the scanner assembly 110 to activate the transmitter circuitry to generate an electrical pulse to excite the selected transducer array element(s), and/or (3) accepting amplified echo signals received from the selected transducer array element(s) via amplifiers included on the integrated circuit controller chip(s) 126 of the scanner assembly 110. In some embodiments, the PIM 104 performs preliminary processing of the echo data prior to relaying the data to the console 106. In examples of such embodiments, the PIM 104 performs amplification, filtering, and/or aggregating of the data. In an embodiment, the PIM 104 also supplies high- and low-voltage DC power to support operation of the device 102 including circuitry within the scanner assembly 110.

The IVUS console 106 receives the echo data from the scanner assembly 110 by way of the PIM 104 and processes the data to reconstruct an image of the tissue structures in the medium surrounding the scanner assembly 110. The console 106 outputs image data such that an image of the vessel 120, such as a cross-sectional image of the vessel 120, is displayed on the monitor 108. Vessel 120 may represent fluid filled or surrounded structures, both natural and man-made. The vessel 120 may be within a body of a patient. The vessel 120 may be a blood vessel, as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be used to examine man-made structures such as, but without limitation, heart valves, stents, shunts, filters and other devices.

Figure 2:
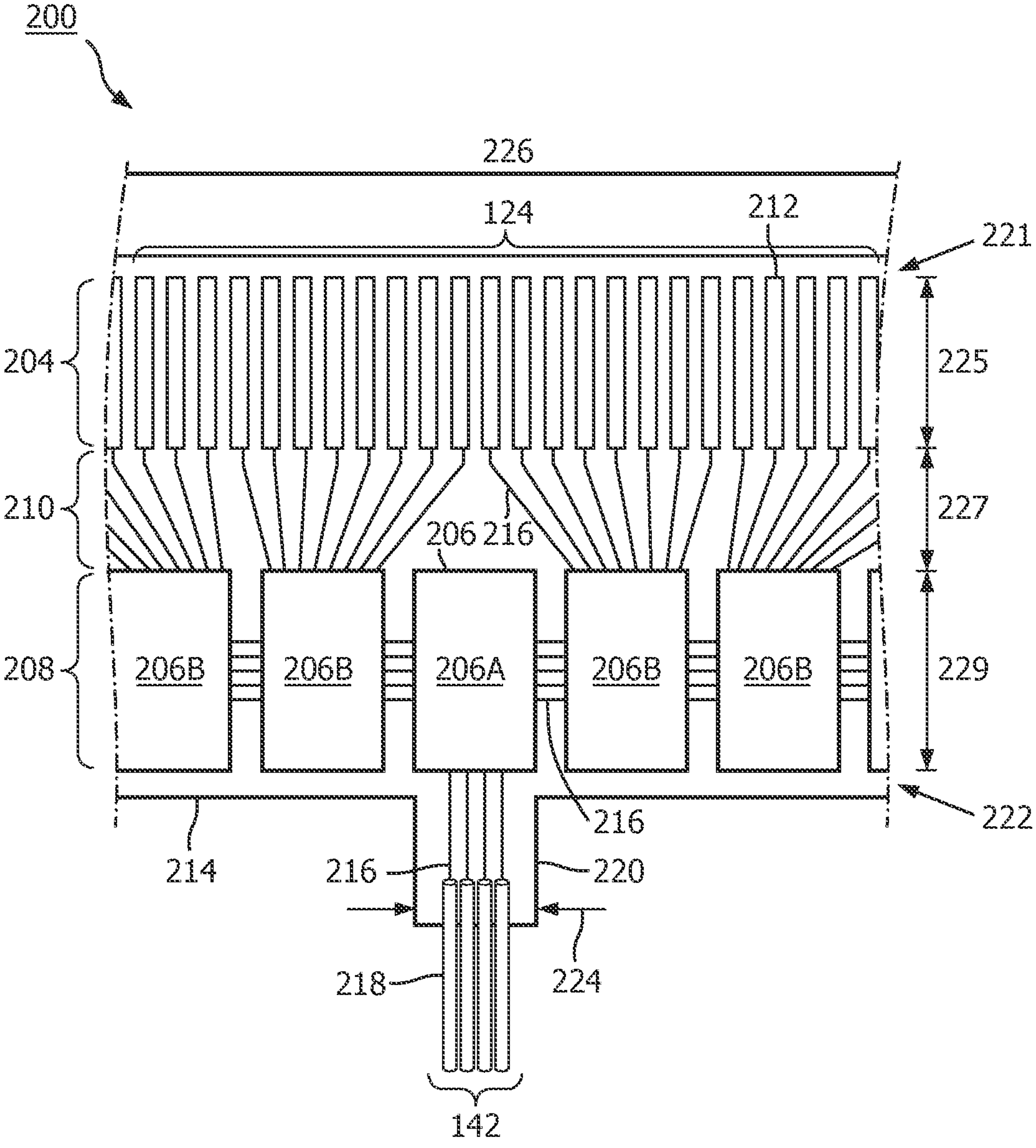
FIG. 2 is a diagrammatic view of the top of a scanner assembly in a flat configuration, according to aspects of the present disclosure.

In some embodiments, the IVUS device includes some features similar to traditional solid-state IVUS catheters, such as the EagleEye® catheter available from Volcano Corporation and those disclosed in U.S. Pat. No. 7,846,101 hereby incorporated by reference in its entirety. For example, the IVUS device 102 includes the scanner assembly 110 near a distal end of the device 102 and a transmission line bundle 112 extending along the longitudinal body of the device 102. The transmission line bundle or cable 112 can include a plurality of conductors, including one, two, three, four, five, six, seven, or more conductors 218 (FIG. 2). It is understood that any suitable gauge wire can be used for the conductors 218. In an embodiment, the cable 112 can include a four-conductor transmission line arrangement with, e.g., 41 American Wire Gauge (AWG) gauge wires. In an embodiment, the cable 112 can include a seven-conductor transmission line arrangement utilizing, e.g., 44 AWG gauge wires. In some embodiments, 43 AWG gauge wires can be used.

The transmission line bundle 112 terminates in a PIM connector 114 at a proximal end of the device 102. The PIM connector 114 electrically couples the transmission line bundle 112 to the PIM 104 and physically couples the IVUS device 102 to the PIM 104. In an embodiment, the IVUS device 102 further includes a guide wire exit port 116. Accordingly, in some instances the IVUS device is a rapid-exchange catheter. The guide wire exit port 116 allows a guide wire 118 to be inserted towards the distal end in order to direct the device 102 through the vessel 120.

In an embodiment, the image processing system 106 generates flow data by processing the echo signals from the IVUS device 102 into Doppler power or velocity information. The image processing system 106 may also generate B-mode data by applying envelope detection and logarithmic compression on the conditioned echo signals. The processing system 106 can further generate images in various views, such as 2D and/or 3D views, based on the flow data or the B-mode data. The processing system 106 can also perform various analyses and/or assessments. For example, the processing system 106 can apply virtual histology (VH) techniques, for example, to analyze or assess plaques within a vessel (e.g., the vessel 120). The images can be generated to display a reconstructed color-coded tissue map of plaque composition superimposed on a cross-sectional view of the vessel.

In an embodiment, the processing system 106 can apply a blood flow detection algorithm (e.g., ChromaFlo) to determine the movement of blood flow, for example, by acquiring image data of a target region (e.g., the vessel 120) repeatedly and determining the movement of the blood flow from the image data. The blood flow detection algorithm operates based on the principle that signals measured from vascular tissue are relatively static from acquisition to acquisition, whereas signals measured from blood flow vary at a characteristic rate corresponding to the flow rate. As such, the blood flow detection algorithm may determine movements of blood flow based on variations in signals measured from the target region between repeated acquisitions. To acquire the image data repeatedly, the processing system 106 may control to the device 102 to transmit repeated pulses on the same aperture.

While the present disclosure refers to intravascular ultrasound (IVUS) imaging using an intravascular catheter or guidewire, it is understood that one or more aspects of the present disclosure can be implemented in any suitable ultrasound imaging system, including a synthetic aperture ultrasound imaging system, a phased array ultrasound imaging system, or any other array-based ultrasound imaging system. For example, aspects of the present disclosure can be implemented in intraluminal ultrasound imaging systems using an intracardiac (ICE) echocardiography catheter and/or a transesophageal echocardiography (TEE) probe, and/or external ultrasound imaging system using an ultrasound probe configured for imaging while positioned adjacent to and/or in contact with the patient's skin. The ultrasound imaging device can be a transthoracic echocardiography (TTE) imaging device in some embodiments.

An ultrasound transducer array of ultrasound imaging device includes an array of acoustic elements configured to emit ultrasound energy and receive echoes corresponding to the emitted ultrasound energy. In some instances, the array may include any number of ultrasound transducer elements. For example, the array can include between 2 acoustic elements and 10000 acoustic elements, including values such as 2 acoustic elements, 4 acoustic elements, acoustic elements, 64 acoustic elements, 128 acoustic elements, 500 acoustic elements, 812 acoustic elements, 3000 acoustic elements, 9000 acoustic elements, and/or other values both larger and smaller. In some instances, the transducer elements of the array may be arranged in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of transducer elements (e.g., one or more rows, one or more columns, and/or one or more orientations) can be uniformly or independently controlled and activated. The array can be configured to obtain one-dimensional, two-dimensional, and/or three-dimensional images of patient anatomy.

The ultrasound transducer elements may comprise piezoelectric/piezoresistive elements, piezoelectric micromachined ultrasound transducer (PMUT) elements, capacitive micromachined ultrasound transducer (CMUT) elements, and/or any other suitable type of ultrasound transducer elements. The ultrasound transducer elements of the array are in communication with (e.g., electrically coupled to) electronic circuitry. For example, the electronic circuitry can include one or more transducer control logic dies. The electronic circuitry can include one or more integrated circuits (IC), such as application specific integrated circuits (ASICs). In some embodiments, one or more of the ICs can comprise a microbeamformer (OF). In other embodiments, one or more of the ICs comprises a multiplexer circuit (MUX).

FIG. 2 is a diagrammatic top view of a portion of a flexible assembly 200, according to aspects of the present disclosure. The flexible assembly 200 includes a transducer array 124 formed in a transducer region 204 and transducer control logic dies 206 (including dies 206A and 206B) formed in a control region 208, with a transition region 210 disposed therebetween.

The transducer control logic dies 206 are mounted on a flexible substrate 214 into which the transducers 212 have been previously integrated. The flexible substrate 214 is shown in a flat configuration in FIG. 2. Though six control logic dies 206 are shown in FIG. 2, any number of control logic dies 206 may be used. For example, one, two, three, four, five, six, seven, eight, nine, ten, or more control logic dies 206 may be used.

The flexible substrate 214, on which the transducer control logic dies 206 and the transducers 212 are mounted, provides structural support and interconnects for electrical coupling. The flexible substrate 214 may be constructed to include a film layer of a flexible polyimide material such as KAPTON™ (trademark of DuPont). Other suitable materials include polyester films, polyimide films, polyethylene napthalate films, or polyetherimide films, liquid crystal polymer, other flexible printed semiconductor substrates as well as products such as Upilex® (registered trademark of Ube Industries) and TEFLON® (registered trademark of E.I. du Pont). In the flat configuration illustrated in FIG. 2, the flexible substrate 214 has a generally rectangular shape. As shown and described herein, the flexible substrate 214 is configured to be wrapped around a support member 230 (FIG. 3) in some instances. Therefore, the thickness of the film layer of the flexible substrate 214 is generally related to the degree of curvature in the final assembled flexible assembly 110. In some embodiments, the film layer is between 5 μm and 100 μm, with some particular embodiments being between 5 μm and 25.1 μm, e.g., 6 μm.

The transducer control logic dies 206 is a non-limiting example of a control circuit. The transducer region 204 is disposed at a distal portion 221 of the flexible substrate 214. The control region 208 is disposed at a proximal portion 222 of the flexible substrate 214. The transition region 210 is disposed between the control region 208 and the transducer region 204. Dimensions of the transducer region 204, the control region 208, and the transition region 210 (e.g., lengths 225, 227, 229) can vary in different embodiments. In some embodiments, the lengths 225, 227, 229 can be substantially similar or, the length 227 of the transition region 210 may be less than lengths 225 and 229, the length 227 of the transition region 210 can be greater than lengths 225, 229 of the transducer region and controller region, respectively.

The control logic dies 206 are not necessarily homogenous. In some embodiments, a single controller is designated a master control logic die 206A and contains the communication interface for cable 142 which may serve as an electrical conductor, e.g., electrical conductor 112, between a processing system, e.g., processing system 106, and the flexible assembly 200. Accordingly, the master control circuit may include control logic that decodes control signals received over the cable 142, transmits control responses over the cable 142, amplifies echo signals, and/or transmits the echo signals over the cable 142. The remaining controllers are slave controllers 206B. The slave controllers 206B may include control logic that drives a transducer 212 to emit an ultrasonic signal and selects a transducer 212 to receive an echo. In the depicted embodiment, the master controller 206A does not directly control any transducers 212. In other embodiments, the master controller 206A drives the same number of transducers 212 as the slave controllers 206B or drives a reduced set of transducers 212 as compared to the slave controllers 206B. In an exemplary embodiment, a single master controller 206A and eight slave controllers 206B are provided with eight transducers assigned to each slave controller 206B.

To electrically interconnect the control logic dies 206 and the transducers 212, in an embodiment, the flexible substrate 214 includes conductive traces 216 formed in the film layer that carry signals between the control logic dies 206 and the transducers 212. In particular, the conductive traces 216 providing communication between the control logic dies 206 and the transducers 212 extend along the flexible substrate 214 within the transition region 210. In some instances, the conductive traces 216 can also facilitate electrical communication between the master controller 206A and the slave controllers 206B. The conductive traces 216 can also provide a set of conductive pads that contact the conductors 218 of cable 142 when the conductors 218 of the cable 142 are mechanically and electrically coupled to the flexible substrate 214. Suitable materials for the conductive traces 216 include copper, gold, aluminum, silver, tantalum, nickel, and tin, and may be deposited on the flexible substrate 214 by processes such as sputtering, plating, and etching. In an embodiment, the flexible substrate 214 includes a chromium adhesion layer. The width and thickness of the conductive traces 216 are selected to provide proper conductivity and resilience when the flexible substrate 214 is rolled. In that regard, an exemplary range for the thickness of a conductive trace 216 and/or conductive pad is between 1-5 μm. For example, in an embodiment, 5 μm conductive traces 216 are separated by 5 μm of space. The width of a conductive trace 216 on the flexible substrate may be further determined by the width of the conductor 218 to be coupled to the trace/pad.

The flexible substrate 214 can include a conductor interface 220 in some embodiments. The conductor interface 220 can be a location of the flexible substrate 214 where the conductors 218 of the cable 142 are coupled to the flexible substrate 214. For example, the bare conductors of the cable 142 are electrically coupled to the flexible substrate 214 at the conductor interface 220. The conductor interface 220 can be tab extending from the main body of flexible substrate 214. In that regard, the main body of the flexible substrate 214 can refer collectively to the transducer region 204, controller region 208, and the transition region 210. In the illustrated embodiment, the conductor interface 220 extends from the proximal portion 222 of the flexible substrate 214. In other embodiments, the conductor interface 220 is positioned at other parts of the flexible substrate 214, such as the distal portion 221, or the flexible substrate 214 may lack the conductor interface 220. A value of a dimension of the tab or conductor interface 220, such as a width 224, can be less than the value of a dimension of the main body of the flexible substrate 214, such as a width 226. In some embodiments, the substrate forming the conductor interface 220 is made of the same material(s) and/or is similarly flexible as the flexible substrate 214. In other embodiments, the conductor interface 220 is made of different materials and/or is comparatively more rigid than the flexible substrate 214. For example, the conductor interface 220 can be made of a plastic, thermoplastic, polymer, hard polymer, etc., including polyoxymethylene (e.g., DELRIN®), polyether ether ketone (PEEK), nylon, Liquid Crystal Polymer (LCP), and/or other suitable materials.

Figure 3:
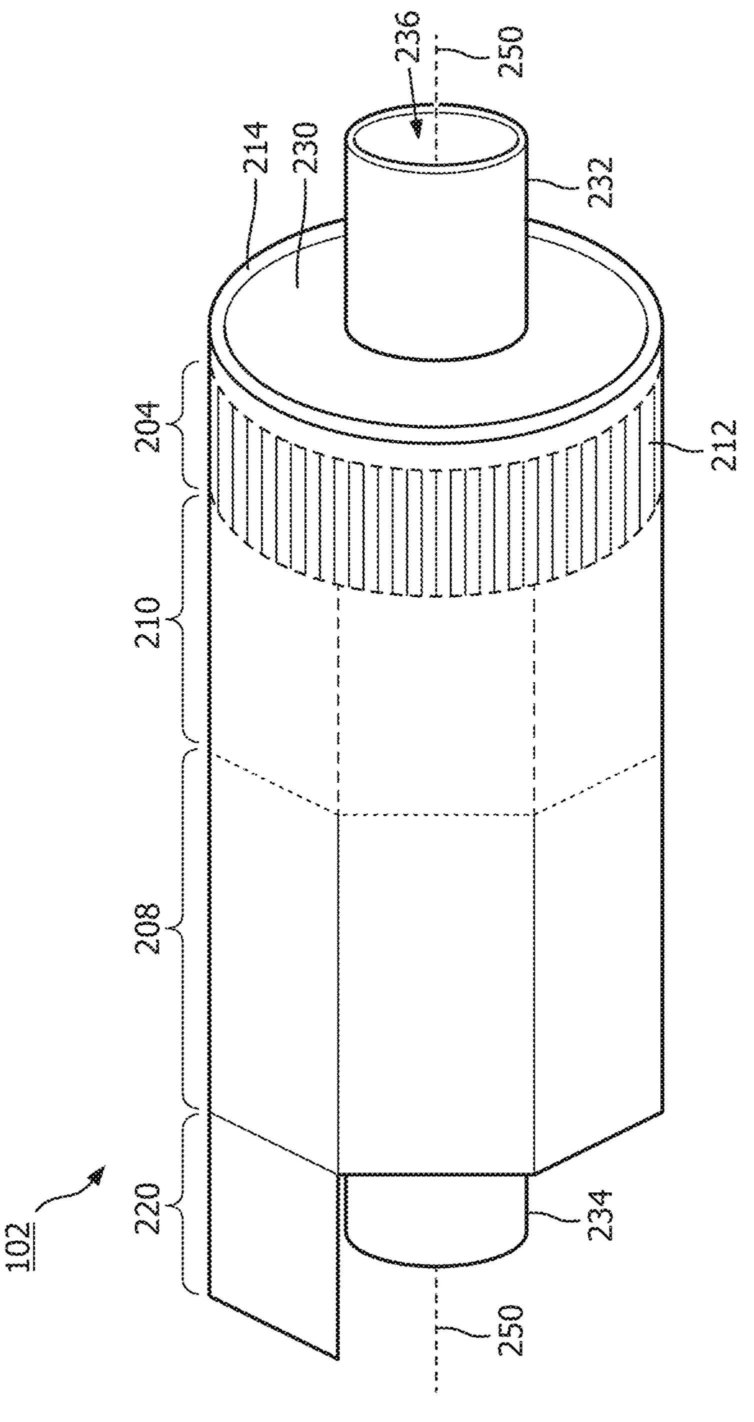
FIG. 3 is a diagrammatic perspective view of the scanner assembly shown in FIG. 2 in a rolled configuration around a support member, according to aspects of the present disclosure.

FIG. 3 illustrates a perspective view of the device 102 with the scanner assembly 110 in a rolled configuration. In some instances, the assembly 110 is transitioned from a flat configuration (FIG. 2) to a rolled or more cylindrical configuration (FIG. 3). For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESOLUTION INTRAVASCULAR ULTRASOUND SENSING ASSEMBLY HAVING A FLEXIBLE SUBSTRATE," each of which is hereby incorporated by reference in its entirety.

In some embodiments, the transducer elements 212 and/or the controllers 206 can be positioned in in an annular configuration, such as a circular configuration or in a polygon configuration, around a longitudinal axis 250 of a support member 230. It will be understood that the longitudinal axis 250 of the support member 230 may also be referred to as the longitudinal axis of the scanner assembly 110, the flexible elongate member 121, and/or the device 102. For example, a cross-sectional profile of the imaging assembly 110 at the transducer elements 212 and/or the controllers 206 can be a circle or a polygon. Any suitable annular polygon shape can be implemented, such as a based on the number of controllers/transducers, flexibility of the controllers/transducers, etc., including a pentagon, hexagon, heptagon, octagon, nonagon, decagon, etc. In some examples, the plurality of transducer controllers 206 may be used for controlling the plurality of ultrasound transducer elements 212 to obtain imaging data associated with the vessel 120.

The support member 230 can be referenced as a unibody in some instances. The support member 230 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, ('220 Application) the entirety of which is hereby incorporated by reference herein. The support member 230 can be a ferrule having a distal flange or portion 232 and a proximal flange or portion 234. The support member 230 can be tubular in shape and define a lumen 236 extending longitudinally therethrough. The lumen 236 can be sized and shaped to receive the guide wire 118. The support member 230 can be manufactured using any suitable process. For example, the support member 230 can be machined and/or electrochemically machined or laser milled, such as by removing material from a blank to shape the support member 230, or molded, such as by an injection molding process.

Figure 4:
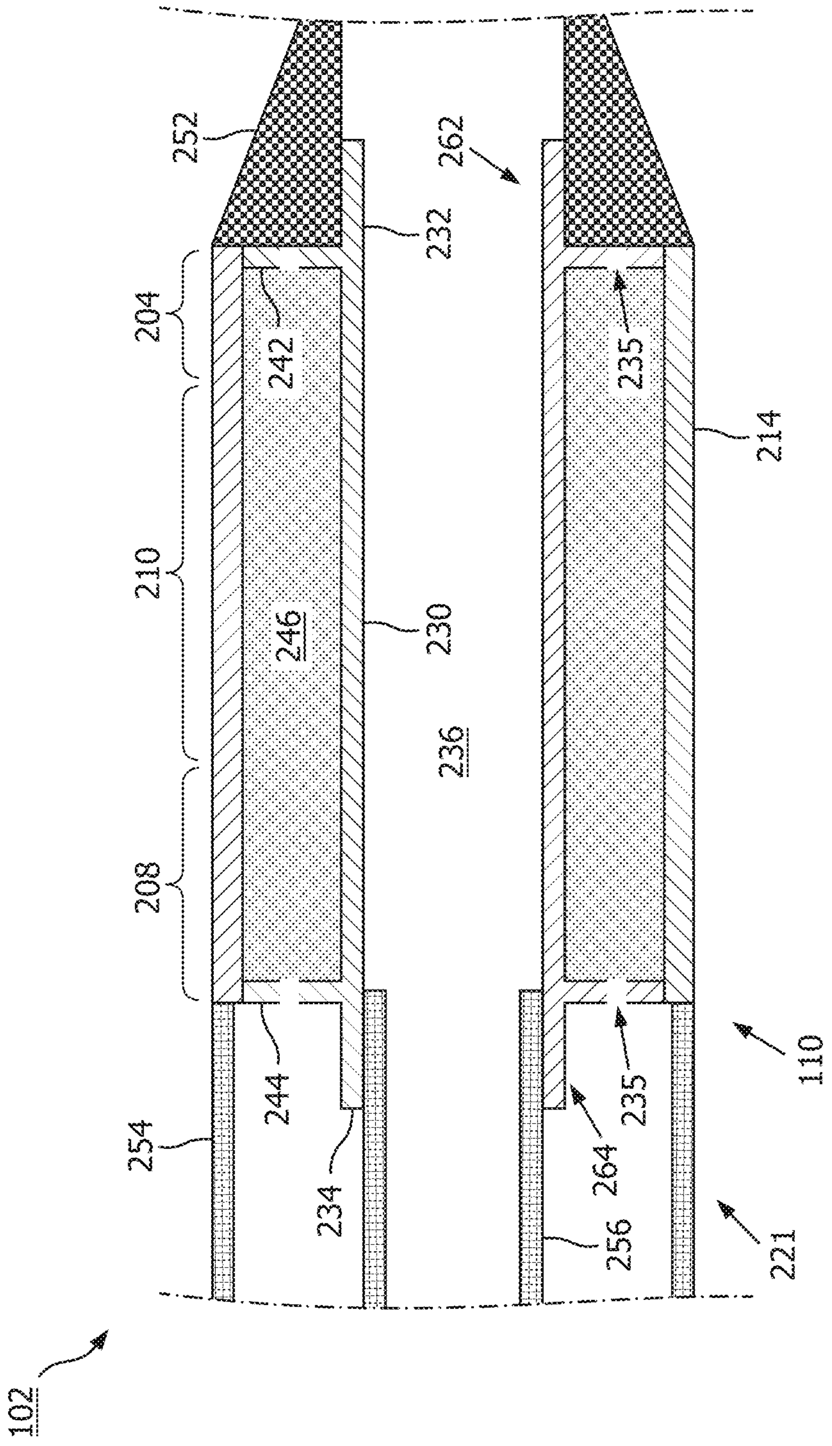
FIG. 4 is a diagrammatic cross-sectional side view of a scanner assembly in a rolled configuration around a support member, according to aspects of the present disclosure.

Referring now to FIG. 4, shown there is a diagrammatic cross-sectional side view of a distal portion of the intraluminal imaging device 102, including the flexible substrate 214 and the support member 230, according to aspects of the present disclosure. The support member 230 can be referenced as a unibody in some instances. The support member 230 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, the entirety of which is hereby incorporated by reference herein. The support member 230 can be ferrule having a distal portion 262 and a proximal portion 264. The support member 230 can define a lumen 236 extending along the longitudinal axis LA. The lumen 236 is in communication with the entry/exit port 116 and is sized and shaped to receive the guide wire 118 (FIG. 1). The support member 230 can be manufactured according to any suitable process. For example, the support member 230 can be machined and/or electrochemically machined or laser milled, such as by removing material from a blank to shape the support member 230, or molded, such as by an injection molding process. In some embodiments, the support member 230 may be integrally formed as a unitary structure, while in other embodiments the support member 230 may be formed of different components, such as a ferrule and stands 242, 244, that are fixedly coupled to one another. In some cases, the support member 230 and/or one or more components thereof may be completely integrated with inner member 256. In some cases, the inner member 256 and the support member 230 may be joined as one, e.g., in the case of a polymer support member.

Stands 242, 244 that extend vertically are provided at the distal and proximal portions 262, 264, respectively, of the support member 230. The stands 242, 244 elevate and support the distal and proximal portions of the flexible substrate 214. In that regard, portions of the flexible substrate 214, such as the transducer portion 204 (or transducer region 204), can be spaced from a central body portion of the support member 230 extending between the stands 242, 244. The stands 242, 244 can have the same outer diameter or different outer diameters. For example, the distal stand 242 can have a larger or smaller outer diameter than the proximal stand 244 and can also have special features for rotational alignment as well as control chip placement and connection. To improve acoustic performance, any cavities between the flexible substrate 214 and the surface of the support member 230 are filled with a backing material 246. The liquid backing material 246 can be introduced between the flexible substrate 214 and the support member 230 via passageways 235 in the stands 242, 244. In some embodiments, suction can be applied via the passageways 235 of one of the stands 242, 244, while the liquid backing material 246 is fed between the flexible substrate 214 and the support member 230 via the passageways 235 of the other of the stands 242, 244. The backing material can be cured to allow it to solidify and set. In various embodiments, the support member 230 includes more than two stands 242, 244, only one of the stands 242, 244, or neither of the stands. In that regard the support member 230 can have an increased diameter distal portion 262 and/or increased diameter proximal portion 264 that is sized and shaped to elevate and support the distal and/or proximal portions of the flexible substrate 214.

The support member 230 can be substantially cylindrical in some embodiments. Other shapes of the support member 230 are also contemplated including geometrical, non-geometrical, symmetrical, non-symmetrical, cross-sectional profiles. As the term is used herein, the shape of the support member 230 may reference a cross-sectional profile of the support member 230. Different portions the support member 230 can be variously shaped in other embodiments. For example, the proximal portion 264 can have a larger outer diameter than the outer diameters of the distal portion 262 or a central portion extending between the distal and proximal portions 262, 264. In some embodiments, an inner diameter of the support member 230 (e.g., the diameter of the lumen 236) can correspondingly increase or decrease as the outer diameter changes. In other embodiments, the inner diameter of the support member 230 remains the same despite variations in the outer diameter.

A proximal inner member 256 and a proximal outer member 254 are coupled to the proximal portion 264 of the support member 230. The proximal inner member 256 and/or the proximal outer member 254 can comprise a flexible elongate member. The proximal inner member 256 can be received within a proximal flange 234. The proximal outer member 254 abuts and is in contact with the flexible substrate 214. A distal member 252 is coupled to the distal portion 262 of the support member 230. For example, the distal member 252 is positioned around the distal flange 232. The distal member 252 can abut and be in contact with the flexible substrate 214 and the stand 242. The distal member 252 can be the distal-most component of the intraluminal imaging device 102.

One or more adhesives can be disposed between various components at the distal portion of the intraluminal imaging device 102. For example, one or more of the flexible substrate 214, the support member 230, the distal member 252, the proximal inner member 256, and/or the proximal outer member 254 can be coupled to one another via an adhesive.

Figure 5:
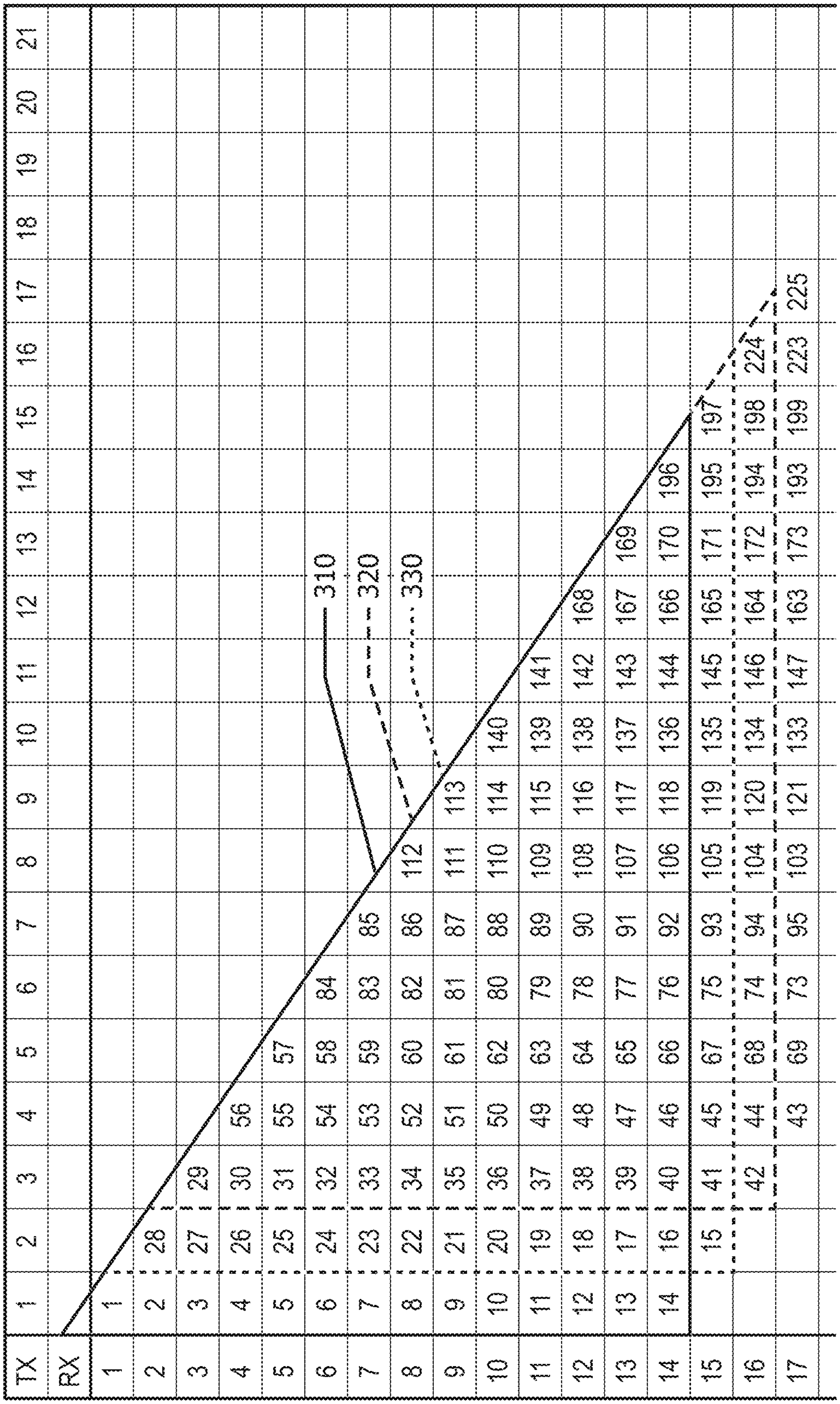
FIG. 5 is a diagrammatic graphical view of an ultrasound pulse sequence, according to aspects of the present disclosure.

FIG. 5 is a diagrammatic graphical view showing an ultrasound pulse sequence of a solid-state IVUS device. The pulse sequence 300 comprises a contiguous "zig-zag" pattern or arrangement of transmit-receive pairs, which can alternatively be described as transmit-receive events. Each transmit-receive pair is represented by an index, or number, corresponding to a sequential time at which the corresponding transmit-receive pair is activated to obtain ultrasound imaging data. In that regard, each transmit-receive index is an integer representing its relative temporal position in the sequence 300. In the embodiment of FIG. 5, each transmit-receive index corresponds to a single transmit-receive pair. Each transmit-receive pair is defined by a transmit element index, shown on the x-axis, and a receive element index, shown on the y-axis. Each transmit element index and receive element index corresponds to an ultrasound element of an array of ultrasound transducer elements. In the embodiment shown in FIG. 5, the array comprises 64 ultrasound transducer elements.

For example, the transmit-receive pair associated with transmit-receive index "1" is defined by transmit element index number 1 and receive element index 1. In some embodiments, the transmit element index and receive element index correspond to the same ultrasound transducer element. In other embodiments, the transmit element index and receive element index correspond to different ultrasound transducer elements. For example, the transmit-receive pair numbered "2," which is shown directly below transmit-receive pair 1, is defined by transmit element index 1 and receive element index 2. That is, the ultrasound imaging data associated with transmit-receive pair 2 is obtained by activating transmit element index 1 to transmit ultrasound energy into the patient volume, and then activating receive element index 2 to receive ultrasound echoes from the patient volume. In FIG. 5, 294 transmit-receive pairs of an ultrasound pulse sequence are shown. Each transmit-receive pair is activated sequentially according to its transmit-receive index.

In the sequence 300, the ultrasound transducer element associated with transmit index 1 transmits 14 consecutive times, while the elements associated with receive indices 1 through 14 are sequentially activated to receive the corresponding echoes. Next, the element associated with transmit index 2 transmits 14 consecutive times, while the elements associated with receive indices 15 through 2 (stepping backward) are sequentially activated to receive the corresponding echoes. This sequence continues in a zig-zag pattern around the array of ultrasound transducer elements. Each transmit-receive pair is associated with one or more apertures 310, 320, 330. For example, a first aperture 310 comprises transmit-receive pairs spanning from index 1 to index 196, a second aperture 320 comprises transmit-receive pairs spanning from index 15 to index 197, and a third aperture 330 comprises transmit-receive pairs spanning from index 29 to index 224. The transmit-receive pairs in each aperture are combined to form an A-line for a B-mode image. Thus, the transmit-receive pairs contained within the first aperture 310 are combined to form a first A-line, the transmit-receive pairs contained within the second aperture 320 are combined to form a second A-line, the transmit-receive pairs contained within the third aperture are combined to form a third A-line, and so on. The A-line formed by the first aperture 310 will be centered between transmit and receive element indices 7 and 8, the A-line formed by the second aperture 320 will be centered between transmit and receive element indices numbered 8 and 9, the A-line formed by the third aperture 330 will be centered between transmit and receive element indices numbered 9 and 10, and so on. Several apertures are used to form A-lines, which are combined and arranged to form a B-mode image.

Figure 9:
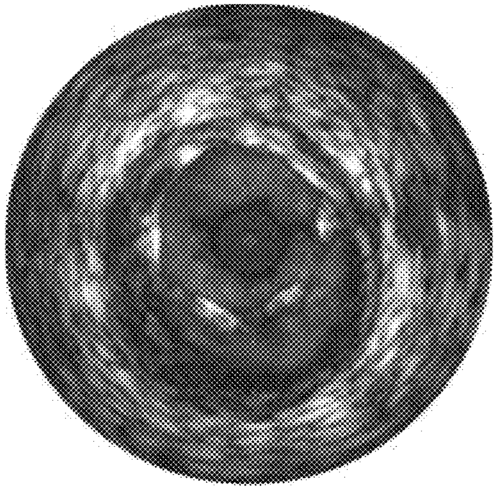
FIG. 9 is a combined B-mode/flow image obtained using a flow scan sequence, according to aspects of the present disclosure.

Scan sequences such as those described above, which produce B-mode images can be combined with flow scan sequences in order to indicate motion in the B-mode image. For example, data collected from a flow scan sequence can be used to modify a corresponding B-mode image to show which areas or pixels in the image are moving. In some embodiments, the B-mode images are modified by coloring the regions or pixels of the images at which motion is detected by the flow data. In some embodiments, a separate flow image can be generated which can be displayed separate from, or overlaid on, a corresponding B-mode image frame. One example of a combined B-mode/flow image is a ChromaFlo® imaging used in Philips™ IVUS imaging catheters. An example of a ChromaFlo® image 400 is shown in FIG. 9, which is described further below.

Some flow scan sequences involve several consecutive or contiguous firings of a single subset of acoustic elements of an array, incrementing the subset of acoustic elements by one acoustic element, and repeating the pattern until all subsets of acoustic elements of the array have been fired several times. Such scan sequences are described further below with respect to FIGS. 7 and 8. The subsets of acoustic elements used in the flow scan sequences are referred to as subapertures. In an exemplary embodiment, a subaperture for a flow scan sequence, as opposed to a B-mode imaging scan sequence, comprises a group of contiguous acoustic elements which are simultaneously fired to transmit ultrasonic energy into an anatomy, and receive ultrasonic echoes corresponding to the transmitted ultrasonic energy. These subapertures are illustrated in FIGS. 6A-6C.

Figure 6B:
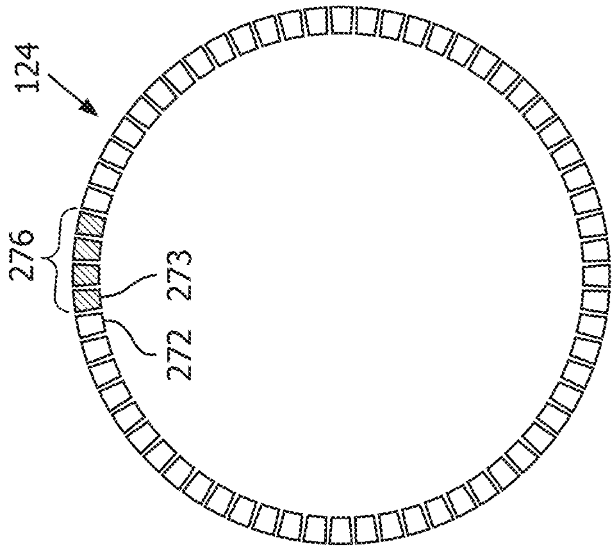
FIGS. 6A, 6B and 6C are diagrammatic views of an annular array of acoustic elements with different subapertures activated, according to aspects of the present disclosure.
Figure 6C:
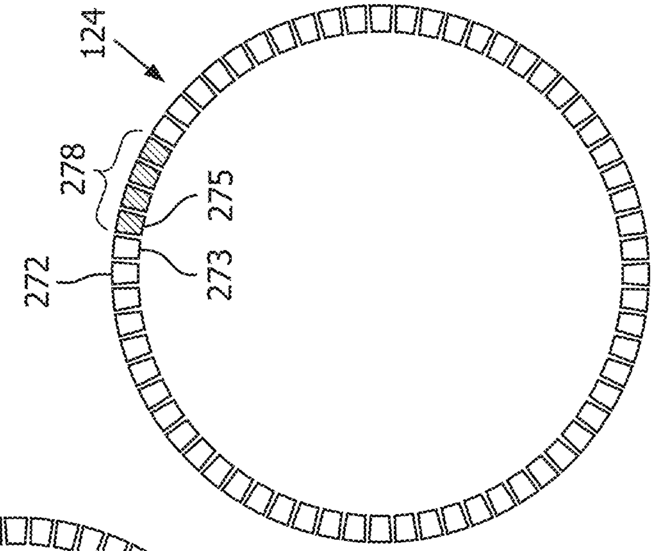
Figure 6A:
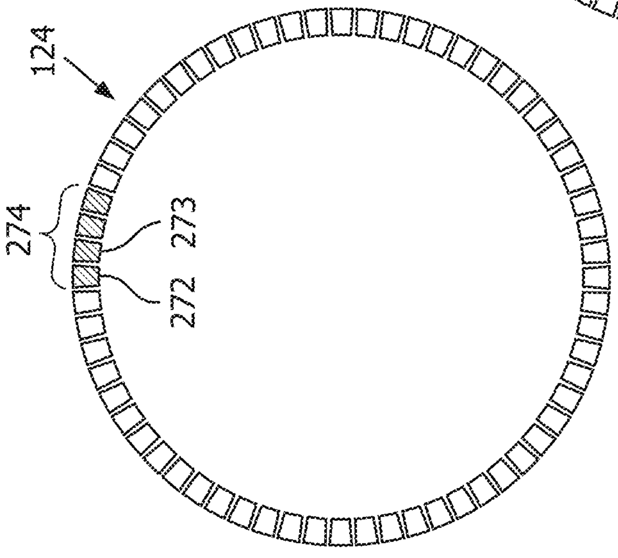

FIGS. 6A-6C are diagrammatic cross-sectional views of the array 124 of the imaging device 102 with different four-element subapertures activated, according to an embodiment of the present disclosure. In that regard, FIG. 6A illustrates the array 124 with a first subaperture 274 activated. The first subaperture 274 comprises four acoustic elements, which are shown with shading. The first subaperture 274 includes an acoustic element 272, and three additional contiguous acoustic elements in the clockwise direction. In some embodiments, the acoustic elements of the first subaperture 274 are activated simultaneously to transmit and/or receive acoustic energy. In other embodiments, only one or a portion of the acoustic elements of the first subaperture 274 are activated at a time, and are later combined using, for example, delay-and-sum beamforming. Furthermore, although the first subaperture 274 is shown comprising four acoustic elements, the first subaperture 274 can comprise fewer or more acoustic elements, such as one, two, three, five, six, ten, or any suitable number of acoustic elements.

In one aspect, the position of the four-element first subaperture 274 can be described as having a position index of 64, corresponding to the acoustic element 272. Thus, in some embodiments, the position of a four-element subaperture can be referenced or described by the element number (or index) of the first acoustic element in the subaperture in the clockwise direction. However, in other embodiments, the position of a subaperture can be described by the index of the last acoustic element in the subaperture in the clockwise direction, the index of a middle acoustic element in the subaperture, or any other suitable number. In FIG. 6A, the position of the first subaperture 274 can be described as having a position of 64, referring to the $64^{th}$ element in the array 124, which is the first acoustic element in the subaperture in the clockwise direction.

FIG. 6B illustrates the array 124 with a second subaperture 276 activated. The second subaperture has a position index of 1, corresponding to the acoustic element 273, which is the first acoustic element in the array 124. Thus, the second subaperture 276 is advanced one acoustic element in the clockwise direction, such that the first and second subapertures 274, 276 comprise three of the same acoustic elements of the array. FIG. 6C illustrates the array 124 with a third subaperture 278 activated. The third subaperture 278 has a position index of 2, corresponding to the acoustic element 275, which is the second acoustic element in the array 124. Thus, the third subaperture 278 is advanced one acoustic element in the clockwise direction, such that the second and third subapertures 276, 278 share three of the same acoustic elements.

Figure 8:
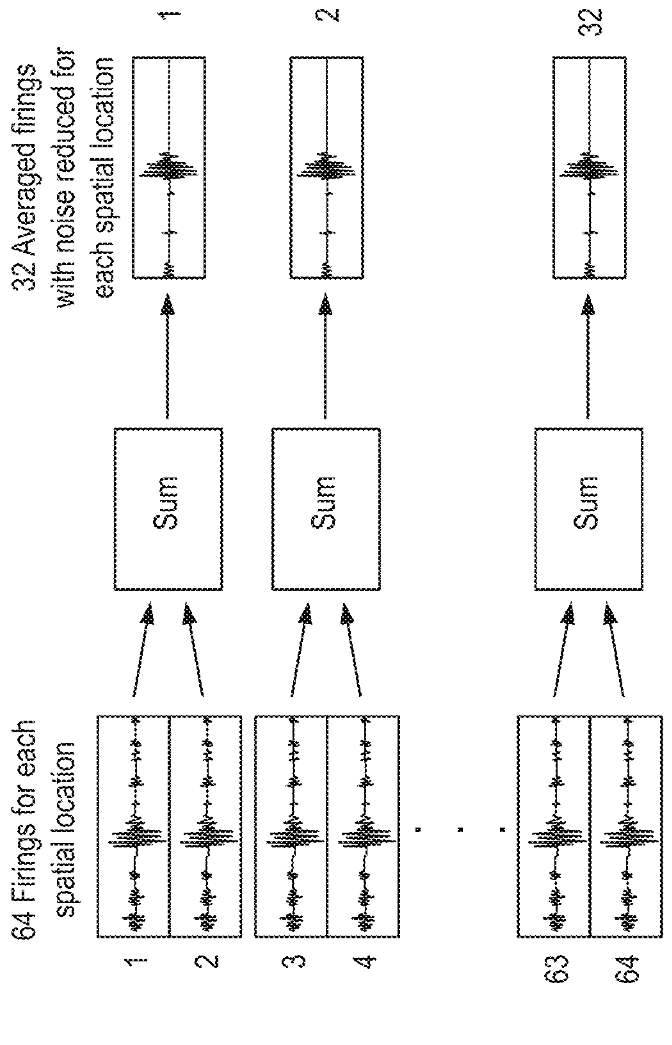
FIG. 8 is a diagrammatic view of a subaperture pulse averaging process, according to aspects of the present disclosure.

It will be understood that the imaging device 102 can activate, during a flow scan sequence, several four-element apertures in a circular or partial-circular pattern. For example, in some embodiments, a flow scan sequence can include activating every four-element subaperture of the array in a circular fashion, such that the pattern can continue for several cycles or circles around the array (i.e., subaperture index 1, 2, 3 . . . 64, 1, 2, 3 . . . etc.) In other embodiments, the scan sequence can include activating subapertures in partial-circle intervals, eventually activating each subaperture of the array a plurality of times. In that regard, activating each subaperture of the array at least twice can be desirable in order to detect and/or measure movement of fluids or structures in an image. However, in some embodiments of a flow scan sequence, only some of the subapertures are activated. FIGS. 7 and 8 illustrate conventional flow scan sequences. FIGS. 11-15 illustrate various interleaved full-circle and partial-circle scan sequences, according to embodiments of the present disclosure.

The scan sequences illustrated in FIGS. 7, 8, and 11-15 can be described by a number of characteristics, including pulse repetition interval (PRI), interleave pulse repetition interval (interval PRI), ensemble length, dwell time, and other characteristics. For example, PRI can be described as a time interval between one subaperture firing and the next. For simplicity, it can be assumed that all PRI's in a scan sequence are of uniform duration, though this is not necessary. The interleave PRI can be described as the time interval between successive firings of a same subaperture. Thus, when there are n firings (i.e. interleave ratio) between successive firings of any given subaperture, the interval PRI can be defined as n*(PRI). The ensemble length can be described as the number of times a subaperture is fired in a scan sequence to achieve one frame or image. It will be understood that the total number of firings of a scan sequence can be equal to the ensemble length times the number of subapertures or acoustic elements in an array. The dwell time can be described as an elapsed time between the first and last subaperture firings of a subaperture at a given location. Dwell time can be related to ensemble length according to the relationship dwell time=(ensemble length−1)*n*(PRI). Adjusting these characteristics of the scan sequence can affect the flow image or flow information provided by the scan sequence. For example, increasing the dwell time can increase sensitivity to slow moving fluid. Increasing ensemble length can increase the signal-to-noise ratio (SNR) and decrease the variance of a phase estimation (described further below) or power Doppler estimation. Increasing the PRI can increase the maximum imaging depth.

FIG. 7 is a diagram illustrating a flow scan sequence 300 performed by a 64-element array. The scan sequence 300 is performed by activating or firing each subaperture of the array 64 times before advancing to the next subaperture. The scan sequence 300 progresses by advancing the subapertures a single acoustic element at a time. The scan sequence 300 completes one full circle around the array for each flow image or frame. The total amount of firings for the scan sequence is 64×64=4096. The interleave pulse repetition interval, that is, the time between consecutive firings of any one subaperture, is one. The ensemble length, which is the number of times a given subaperture is fired to acquire one flow frame, is 64. FIG. 8 shows an averaging operation 350 that can be performed in a flow scan sequence for the firings of one of the subapertures. The averaging operation 350 includes summing and/or averaging neighboring firings of the 64-firings of the subaperture to create 32 averaged firings. Averaging the firings can reduce noise, thereby improving the signal-to-noise ratio (SNR). The averaged firings are then compared using an RF-based motion detection algorithm that includes a high-pass filter to detect motion in the image. The detected motion information obtained by the high-pass filtering can then be used to either modify (e.g., color) portions of a B-mode image, or to create a separate flow image that can be shown beside, or overlaid on the B-mode image. FIG. 9 is an IVUS image 400 that includes a B-mode image with flow information obtained by the flow scan sequence modifying the B-mode image to illustrate blood flow in a lumen. In particular, the image 400 of FIG. 9 is a ChromaFlo® image provided by a Philips™ IVUS catheter.

The scan sequence 300 illustrated in FIG. 7 has a number of characteristics. While the relatively large ensemble length (64 firings) can improve SNR, and the short interval PRI can increase sensitivity to very fast-moving fluid, the same characteristics also mean that a large number of firings are required, and the amount of time between firings of any single subaperture is very short. Accordingly, the scan sequence 300 of FIG. 7 limits the frame rate of the flow frames and is limited in sensitivity to slower moving fluids.

Figure 10:
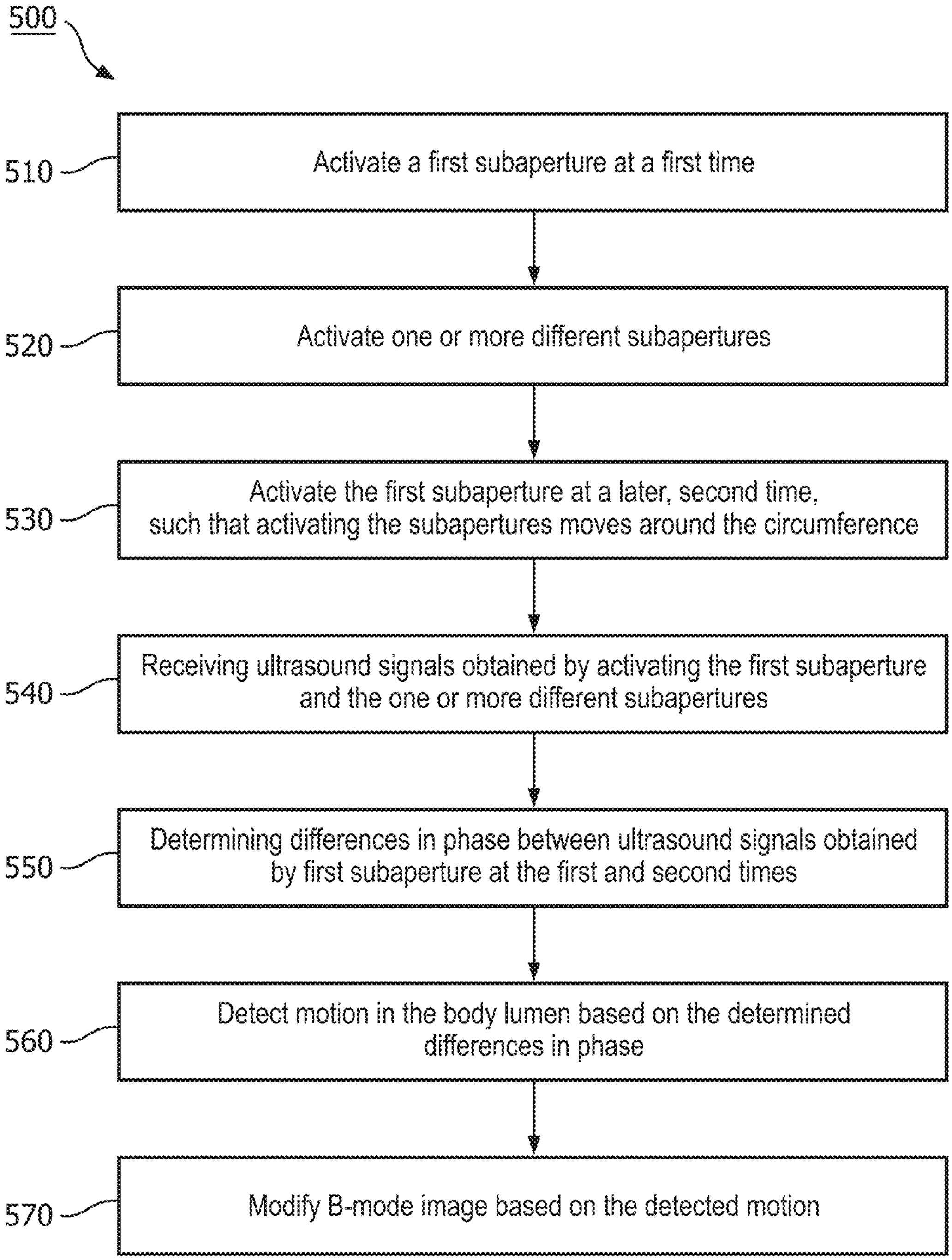
FIG. 10 is a flow chart illustrating an interleaved flow scan sequence, according to aspects of the present disclosure.

The present disclosure provides various scan sequences that include interleaving full-circle and partial-circle sequences of subaperture firings that can improve frame rates of flow images and/or improve sensitivity to slower-moving fluids and structures in a field of view. It will be understood that the term "interleaving," when used to describe the methods and scan sequences below, is used in a different manner than described above with respect to interleaving flow scan sequences with standard imaging sequences. In that regard, FIG. 10 is a flow diagram illustrating a method 500 for performing a flow scan sequence comprising an interleaved sequence or pattern of subaperture firings. The scan sequence of the method 500 can, for example, increase the interleave PRI between firings of a given subaperture (therefore increasing dwell time if the ensemble length remains the same) in order to increase sensitivity to slower moving fluids. Furthermore, the scan sequence of interleaved subaperture firings can reduce the number of firings required to generate a single flow frame (same dwell time with reduced ensemble length), thus increasing the achievable flow frame rates. These advantages can be achieved by the scan sequence without a significant negative effect on SNR or image quality.

In step 510, a first subaperture comprising a first subset of acoustic elements of an annular array is activated or fired at a first time to transmit ultrasonic energy into an anatomy, such as a blood vessel, and receive echoes corresponding to the transmitted ultrasonic energy. The first subaperture can be activated by a processor. In some embodiments, the processor can be part of an ultrasound probe, such as an IVUS imaging catheter. For example, the first subaperture can be activated by one or more of the ASICs of the imaging device 102 shown in FIG. 2. In other embodiments, the first subaperture can be activated by a processor of a central console. The first subaperture, and some or all of the other subapertures, can comprise consecutive or contiguous subsets of acoustic elements, in some embodiments. In other embodiments, the subapertures can comprise non-consecutive, or non-contiguous subsets of acoustic elements. In an exemplary embodiment, each subaperture comprises a group of four contiguous acoustic elements that are simultaneously activated. However, fewer or more acoustic elements can be included in each subaperture, such as 1, 2, 3, 5, 6, 7, 10, or any suitable number of acoustic elements. As explained above, the position or position index of the subaperture can be described by the index of the first acoustic element of the subaperture in the clockwise direction. However, in some embodiments, the position of the subaperture can be described by the last element of the subaperture in the clockwise direction, an intermediate element of the subaperture in the clockwise direction, or any other suitable element of the subaperture. Furthermore, in some embodiments, the elements of each subaperture are activated separately and summed, aggregated, or combined.

In step 520, one or more different subapertures are activated after activating the first subaperture at the first time. In some embodiments, the one or more different subapertures are activated immediately after activating the first subaperture, such that the activations of the first subaperture and the one or more different subapertures are adjacent in time. As explained further below, in some embodiments in which an annular array is used, all other subapertures are activated in a circular fashion around the annular array (i.e. full-circle interleave). In other embodiments, only a portion of the other subapertures are activated. For example, a portion of the other subapertures defining an angular portion of an annular array can be activated a plurality of times (i.e. partial-circle interleave). In step 530, the first subaperture is activated again at a later, second time, only after the one or more other subapertures have been activated. Accordingly, the one or more other subapertures that are activated between successive firings of the first subapertures are interleaving subapertures, and the interleave PRI between firings the first subaperture (and any other subaperture) is greater than one subaperture firing.

In step 540, ultrasound signals obtained by the first subaperture and other subapertures are received by the processor, and in step 550, the ultrasound signals obtained by the first subaperture at the first and second times are analyzed to determine a difference in phase between the signals. In step 560, motion in the fluid is detected based on the determined difference in phase between the signals. In some embodiments, analyzing the ultrasound signals comprises using a phase-based motion detector algorithm according to the relationship below:

$$\varphi(r, \theta) = \angle \left\{ LPF\left( \sum_i rf_i * rf_{i+\Delta}^* \right) \right\}$$

Where $rf_i$ denotes complex radiofrequency (rf) data from an $i^{th}$ transmit, $rf_{i+\Delta}$ is the conjugate transpose of the complex rf data $\Delta$ transmits separated from $rf_i$, and LPF is the spatial low-pass filter for more robust phase estimation. By measuring the phase changes in rf lines acquired by the same subaperture but at different times, a phase map can be generated which may show no or negligible phase changes in the vessel tissue region but meaningful phase changes in the lumen where blood motion is present. A phase angle estimator estimates the relative phase shift between successive echoes relative to the nominal receive center frequency. In some embodiments, quadrature demodulation is applied to the echoes, and the phase is estimated with the standard Kasai estimator, as described in Kasai, et al., "Real-Time Two-Dimensional Blood Flow Imaging Using an Autocorrelation Technique," IEEE Transactions on Sonics and Ultrasonics, vol. SU-32, No. 3, May 1985 ("Kasai"), the entirety of which is hereby incorporated by reference. It will be understood that, when using the above method in an IVUS array, high-pass wall filtering is not necessary as the blood backscatter is quite significant at higher frequencies (e.g., >20 MHz). In other embodiments, a different type of estimator can be used to identify and image moving fluid, such as a Doppler variance estimator. For example, Kasai explains that a Doppler variance estimator can be of the form:

$$\sigma^2 \cong \frac{2}{T^2}\left\{1 - \frac{A(\tau)}{A(0)}\right\} = \frac{2}{T^2}\left\{1 - \frac{|R(T)|}{R(0)}\right\}$$

where $\sigma^2$ is the variance and T denotes the emission interval of ultrasonic pulses. In some aspects, a high pass filter and amplitude estimation such as power Doppler could be used to further increase the interval PRI.

In step 570, a B-mode image obtained by the array is modified based on the detected motion. For example, in one example, the phase map can be used to modify one or more pixels of the B-mode image in order to indicate detected motion in the one or more pixels. For example, the processor may apply a color, including a hue and intensity, to the one or more pixels. In other embodiments, a separate flow image is generated based on the detected motion which can be displayed separately, or overlaid on the B-mode image.

It will be understood that, while the method 500 refers specifically to signals from the first subaperture, detecting motion around an annular array requires comparing different firings of each subaperture. Additionally, although only two successive firings of the first subaperture are mentioned, in practice, more firings may be performed for each subaperture. For example, 3, 4, 6, 8, 10, 32, or any suitable number of firings can be performed for each subaperture. Thus, the phase-based motion detector can analyze signals obtained by each subaperture in the array over several successive firings.

Furthermore, it will be understood that averaging can be used to average two or more successive firings of each aperture in order to increase SNR. Thus, in some embodiments, the system can average signals obtained from firings of a subaperture at first and second times, and firings obtained at third and fourth times, where the first, second, third, and fourth times are consecutive and arranged from earliest to latest.

Additionally, the method can further include segmenting the signals to suppress phase (or variance) signals arising from thermal noise. For instance, low power echoes arising from noise can be segmented and suppressed.

FIGS. 11-15 illustrate interleaved scan sequences for flow imaging. In particular, FIG. 11 illustrates a full-circle interleave sequence 610 for a 64-element annular array. In the full-circle interleave sequence 610, each subaperture 101 of the array is activated in a circular pattern around the annular array. Between successive firings of a same subaperture, all of the other subapertures of the array are activated once before returning to a same subaperture. This pattern is repeated N times, such that each subaperture is activated or fired N times during the scan sequence used to form a single flow frame. Accordingly, the ensemble length, which is the number of times each subaperture is fired during the sequence, is N firings. The interval PRI, which is the amount of time between firings of a same subaperture, is 64 firings. This is a 64× increase in interval PRI from the sequence 300 shown in FIG. 7. Accordingly, the sequence 610 of FIG. 11 can increase the ability of the system to detect motion in slow-moving fluids. For example, in some embodiments, the sequence 610 can enable the system of detect fluid moving slower than 2 cm/sec. Furthermore, the number of total firings required by the sequence 610 can be significantly lower than the number of firings required by the sequence 300 shown in FIG. 7. In FIG. 11, the total number of firings is 64×N firings. In some embodiments of the sequence 610, N is equal to 2, 4, 8, 10, 12, 14, 24, or any other suitable value. In one embodiment, N is equal to 64, and the total number of firings is 4096, similar to the sequence 300 shown in FIG. 7.

In FIG. 12, a partial-circle interleave flow scan sequence 620 is shown. In the partial-circle interleave sequence 620, a group of subapertures 201 forming an angular portion or segment of the annular array (i.e. 1, 2, 3, 4) are activated before returning to the same subaperture. Specifically, contiguous groups of four subapertures are consecutively activated 8 times before advancing to a different group of subapertures comprising a different angular portion or segment of the annular array. The pattern is advanced until each aperture of the array has been activated eight times. In some embodiments, a smaller or larger group of subapertures can be interleaved between firings of a same subaperture, such as 2, 3, 5, 6, 8, 10, or any other suitable number of interleaved subapertures. In the embodiment of the sequence 620 shown in FIG. 12, the interleave PRI is increased 4× compared to the sequence 300 of FIG. 7, while the number of total firings is reduced by a factor of eight. Although the ensemble length is only eight firings in the sequence 620 of FIG. 12, in some embodiments, the partial-circle interleave sequence 620 can offer increased sensitivity to slower moving fluid and increased frame rate (resulting from lower number of firings needed for each frame), without significantly reducing the SNR or quality of the flow image.

In FIG. 13, another embodiment of a partial-circle interleave sequence 630 is shown. In contrast to the partial-circle interleave sequence 620 shown in FIG. 12, the sequence 630 shown in FIG. 13 comprises firing interleaving, non-contiguous groups of subapertures that form an angular portion or segment of the annular array. Each non-contiguous group, in which each subaperture is separated from neighboring subapertures in the group by four subapertures, is activated 8 times before advancing to the next group of non-contiguous subapertures. Advancing to the next group of non-contiguous subapertures comprises advancing at least one subaperture, such that different groups of subapertures interleave one another. Similar to the sequence 620 in FIG. 12, the ensemble length is eight firings, the interleave PRI is four firings, the dwell time is 32 firings, and the total number of firings is 512, thus achieving an 8× increased frame rate compared to the base sequence, with only a small tradeoff in slow flow sensitivity. However, in some embodiments, the sequence 630 in FIG. 13 may result in a flow image having slightly different characteristics than flow images produced by the sequence 620 shown in FIG. 12. For example, one may expect to see discontinuities in the flow image at boundaries between groups of apertures, because different groups of aperture fire at significantly different points in time, and the flow patterns may change between activations of the successive groups. The spatial patterns of such discontinuities will match the spatial arrangement of the groups. For example, in the scheme of FIG. 12, we may see discontinuities with a periodicity of 4 flow lines. In the scheme of FIG. 13, the discontinuity will occur every flow line. This may seem more disruptive may actually be easier to smooth out with a spatial low pass filer. The sequences of FIGS. 12 and 13 may produce images with comparable flow sensitivity. However, when the data are combined to form the images, lateral line-to-line artifacts and discontinuities (e.g., arising from tissue motion, catheter motion, blood decorrelation over time, blood acceleration) may differ.

FIG. 14 shows another example of a full-circle interleave flow scan sequence 640. In the sequence 640 of FIG. 14, non-contiguous groups of subapertures that extend around the annular array are activated, such that the scan sequence makes four circular passes around the annular array in order to activate all subapertures of the annular array once. Neighboring subaperture firings in each pass are separated by four subapertures, such that a group of 16 non-contiguous subapertures are activated in each pass around the annular array. This pattern can be repeated for N passes, such that each subaperture is activated a total of N/4 times. For example, if 16 passes around the annular array are made, the ensemble length of the scan sequence would be four, because it requires four passes or circles around the annular array before the same subaperture is fired again. Similar to the full-circle scan sequence 610 shown in FIG. 11, the interleave PRI of the scan sequence 640 in FIG. 14 is 64 firings. The total number of firings is 16×N, where N is a multiple of four.

FIG. 15 shows another example of a full-circle interleave flow scan sequence 650, which is similar to the sequence 640 shown in FIG. 14, but with consecutive subaperture firings separated by five subapertures, instead of four subapertures. Thus, in the sequence 650 of FIG. 15, it requires five passes around the annular array before returning to any one subaperture. Because the number of elements in the array (64) is not divisible by five, the fifth pass around the annular array includes only 12 subaperture firings, while passes one through four include 13 subaperture firings.

It will be understood that, although the sequences described in FIGS. 11-15 vary in one or more aspects, some features may be included in each of the scan sequences of FIGS. 11-15. For example, each of the scan sequences of FIGS. 11-15 include one or more subaperture firings that are interleaved between successive firings of any same subaperture. This allows lengthening the time between successive firings of a same subaperture (and therefore the dwell time, provided the ensemble length remains constant), while more efficiently scanning the spatial locations around the annular array. These interleaving patterns of subaperture firings can be performed in a full-circle or partial-circle pattern. However, each of the different scan sequences described may provide specific advantages, and may provide images having different characteristics, such as the amount of motion detected, the presence of image artifacts, etc.

Figure 16A:
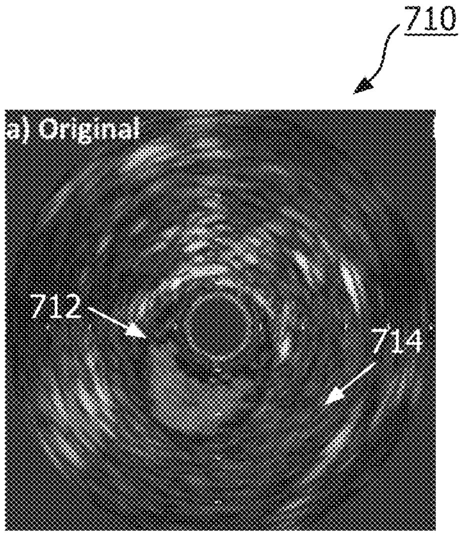
FIGS. 16A, 16B, 16C and 16D are combined B-mode/doppler images generated using different flow scan sequences, according to aspects of the present disclosure.

FIGS. 16A-16D are combined B-mode/flow images obtained by using a plurality of different flow scan sequences. In that regard, FIG. 16A is an image 710 obtained using the scan sequence 300 described with respect to FIG. 7, which employs a power Doppler motion detection algorithm. In that regard, the detected fluid motion region 712 indicated in the image 710 can help identify that region and/or boundary of the lumen in which the blood is flowing. The image 710 also exhibits some artifacts, such as leaking 714, which is the indication of moving blood in an area of the vessel that is unlikely to have actual blood flow. FIG.

Figure 16B:
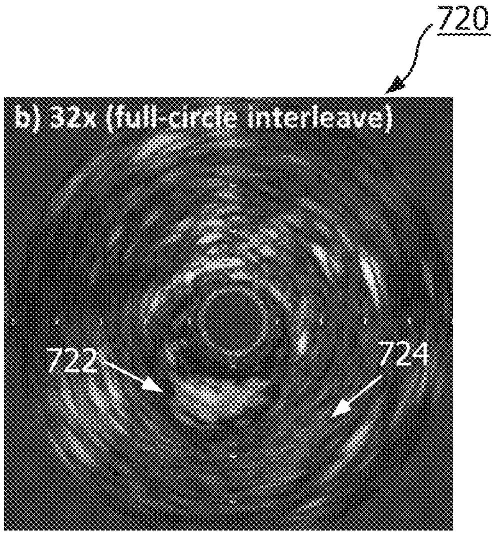

16B is an image 720 that is obtained by a full-circle interleave scan sequence using a phase-based motion detector algorithm, such as the sequence 610 shown in FIG. 11. The image includes 720 similar characteristics to FIG. 16A, and identifies a similar region 722 of flowing blood. However, the image 720 may differ in some respects, such as in the amount of leaking 724 or other flow image artifacts. Additionally, because the scan sequence 610 can provide for higher imaging rates when compared to the sequence 300, the higher frame rate provided by the full-circle interleave scan sequence may be more desirable in some instances, despite potential for increased image artifacts 724. In particular, the ensemble length in FIG. 16*b* is only 2 but the dwell time is the same as in FIG. 16*a*, resulting in a 32× frame rate increase after taking pulse averaging into account.

Figure 16C:
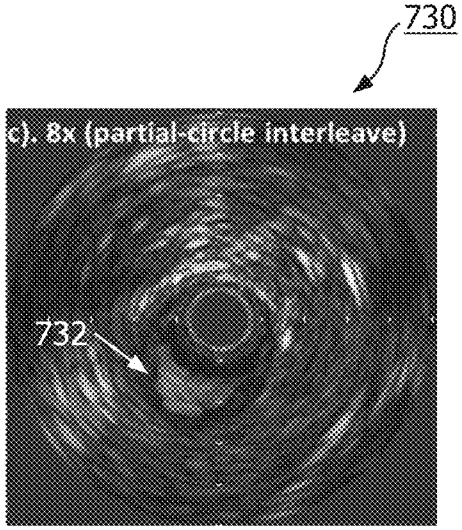
Figure 16D:
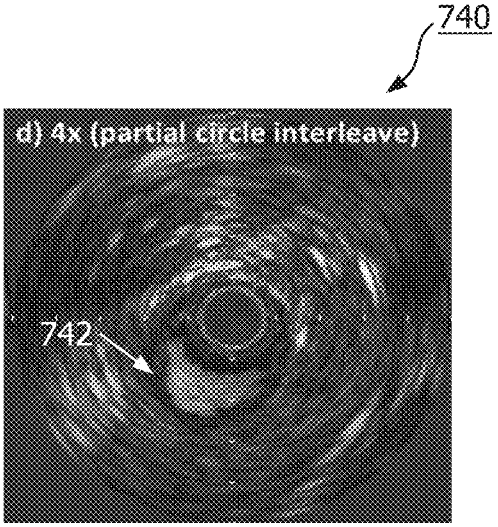

FIG. 16C is a combined B-mode/flow image 730 obtained using a partial-circle interleave sequence, such as the sequence 620 of FIG. 12, with an interleave PRI of eight firings (and same dwell time, thus an 8× increased frame rate of compared to the baseline of FIG. 16*a*). In this image 730, a slightly smaller region 732 of flowing blood is identified when compared with the region 712 of FIG. 16A. Accordingly, the blood flow region 732 of FIG. 16C may not indicate the boundaries of the lumen in the same manner as FIG. 16A. However, FIG. 16C comprises less leaking artifacts when compared with FIG. 16A. FIG. 16D is another image 740 obtained using a partial-circle interleave sequence using a pulse repetition interval of four firings. The dwell time is kept the same, resulting in a 4× frame rate improvement. The sequence used with respect to FIG. 16D indicates a larger blood flow area 742, and decreased leaking artifacts. However, the sequence used to generate the image of FIG. 16D has a twice lower frame rate compared to the image of FIG. 16C.

It will also be understood that one or more of the steps of the methods described above can be performed by one or more components of an ultrasound imaging system, such as the processor, a multiplexer, a beamformer, a signal processing unit, an image processing unit, or any other suitable component of the system. For example, activating the scan sequences may be carried out by a processor in communication with a multiplexer configured to select or activate one or more elements of an ultrasound transducer array. In some embodiments, generating the ultrasound images may include beamforming incoming signals from the ultrasound imaging device and processing the beamformed signals by an image processor. The processing components of the system can be integrated within the ultrasound imaging device, contained within an external console, or may be a separate component.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal ultrasound imaging system, comprising:

an intraluminal catheter or guidewire, comprising:

a flexible elongate member configured to be positioned within a body lumen of a patient;

an annular array of acoustic elements configured to transmit ultrasonic energy into an anatomy and receive echoes corresponding to the transmitted ultrasonic energy, wherein the annular array is positioned around a circumference of the flexible elongate member; and a processor in communication with the annular array and configured to:

activate the annular array to perform a sequence of single transmit firings, wherein the sequence comprises:

a first single transmit firing at a first time by a first subaperture of the annular array, wherein the first subaperture comprises a first subset of the acoustic elements associated with a first portion of the circumference, and wherein the first single transmit firing by the first subaperture occurs only once before the sequence proceeds to a second subaperture comprising a different, second subset of the acoustic elements associated with a different, second portion of the circumference;

a second single transmit firing at a different, second time by the first subaperture, wherein the second single transmit firing occurs only after the sequence has proceeded to the second subaperture;

receive ultrasound signals obtained based on the first single transmit firing at the first time and the second single transmit firing at the second time;

determine temporal differences between the received ultrasound signals;

detect motion in the body lumen based on the determined temporal differences; and output a visual representation of the detected motion to a display in communication with the processor.

2. The intraluminal ultrasound imaging system of claim 1, wherein the processor is configured to activate a plurality of subapertures, including the second subaperture, between the first single transmit firing at the first time and the second single transmit firing at the second time.

3. The intraluminal ultrasound imaging system of claim 2, wherein the processor is configured to activate the plurality of subapertures to complete at least one revolution around the annular array before the second single transmit firing at the second time.

4. The intraluminal ultrasound imaging system of claim 3, wherein the plurality of subapertures comprises all of the subapertures of the annular array except for the first subaperture.

5. The intraluminal ultrasound imaging system of claim 3, wherein the plurality of subapertures comprises a non-consecutive subset of subapertures of the annular array.

6. The intraluminal ultrasound imaging system of claim 5, wherein the non-consecutive subset of the subapertures comprises an interval of M subapertures, wherein a total number of subapertures of the annular array is divisible by M, and wherein the non-consecutive subset of the subapertures is less than the total number of subapertures.

7. The intraluminal ultrasound imaging system of claim 5, wherein the non-consecutive subset of the subapertures comprises an interval of M subapertures, wherein a total number of subapertures of the annular array is not divisible by M, and wherein the non-consecutive subset of the subapertures is less than the total number of subapertures.

8. The intraluminal ultrasound imaging system of claim 2, wherein the processor is configured to activate the plurality of subapertures to complete only part of a revolution around the annular array before the second single transmit firing at the second time.

9. The intraluminal ultrasound imaging system of claim 1, wherein the sequence further comprises:

a third single transmit firing at a third time by the first subaperture and a fourth single transmit firing at a fourth time by the first subaperture, wherein the third time is after the first time and the fourth time is after the second time; and further comprising:

average the received ultrasound signals obtained by the first subaperture at the first time and the third time; and average the received ultrasound signals obtained by the first subaperture at the second time and the fourth time.

10. The intraluminal ultrasound imaging system of claim 1, wherein the processor is further configured to:

activate an imaging sequence to generate an ultrasound image;

generate a flow map based on the detected motion;

modify the ultrasound image by coloring portions of the ultrasound image based on the flow map or overlaying the flow map on the ultrasound image; and output the modified ultrasound image to the display.

11. A method for detecting motion in a body lumen, comprising:

controlling, by a processor, an annular array of acoustic elements in communication with the processor to perform a sequence of single transmit firings, wherein the annular array is coupled to a distal portion of a flexible elongate member configured to be positioned within the body lumen, and wherein the sequence comprises:

a first single transmit firing at a first time by a first subaperture of the annular array, wherein the first subaperture comprises a first subset of the acoustic elements associated with a first portion of the circumference, and wherein the first single transmit firing by the first subaperture occurs only once before the sequence proceeds to a second subaperture comprising a different, second subset of the acoustic elements associated with a different, second portion of the circumference;

a second single transmit firing at a different, second time by the first subaperture, wherein the second single transmit firing occurs only after the sequence has proceeded to the second subaperture;

receiving, at the processor, ultrasound signals obtained based on the first single transmit firing at the first time and the second single transmit firing at the second time;

determining differences in phase between the received ultrasound signals;

detecting motion in the body lumen based on the determined differences in phase; and outputting a visual representation of the detected motion to a display in communication with the processor.

12. The method of claim 11, further comprising activating a plurality of subapertures, including the second subaperture, between the first single transmit firing at the first time and the second single transmit firing at the second time.

13. The method of claim 12, wherein activating the plurality of subapertures comprises activating the plurality of subapertures to complete at least one revolution around the annular array before the second single transmit firing at the second time.

14. The method of claim 13, wherein activating the plurality of subapertures comprises activating all of the subapertures of the annular array except for the first subaperture.

15. The method of claim 13, wherein activating the plurality of subapertures comprises activating a non-consecutive subset of subapertures of the annular array.

16. The method of claim 15, wherein the non-consecutive subset of the subapertures comprises an interval of M subapertures, wherein a total number of subapertures of the annular array is divisible by M, and wherein the non-consecutive subset of the subapertures is less than the total number of subapertures.

17. The method of claim 15, wherein the non-consecutive subset of the subapertures comprises an interval of M subapertures, wherein a total number of subapertures of the annular array is not divisible by M, and wherein the non-consecutive subset of the subapertures is less than the total number of subapertures.

18. The method of claim 12, wherein activating the plurality of subapertures includes activating the plurality of subapertures to complete only part of a revolution around the annular array before the second single transmit firing at the second time.

19. The method of claim 11, wherein the sequence further comprises:

a third single transmit firing at a third time by the first subaperture and a fourth single transmit firing at a fourth time by the first subaperture, wherein the third time is after the first time and the fourth time is after the second time; and further comprising:

averaging the received ultrasound signals obtained by the first subaperture at the first time and the third time; and averaging the received ultrasound signals obtained by the first subaperture at the second time and the fourth time.

20. The method of claim 11, further comprising:

activating an imaging sequence to generate an ultrasound image;

generating a flow map based on the detected motion;

modifying the ultrasound image by coloring portions of the ultrasound image based on the flow map or overlaying the flow map on the ultrasound image; and outputting the modified ultrasound image to the display.

21. The intraluminal ultrasound imaging system of claim 1, wherein the sequence further comprises:

a third single transmit firing by the second subaperture immediately following the first single transmit firing by the first subaperture, and wherein the third single transmit firing by the second subaperture occurs only once before the sequence proceeds to a next subaperture.

* * * * *